(12) United States Patent
Stoessel et al.

(10) Patent No.: US 9,847,499 B2
(45) Date of Patent: Dec. 19, 2017

(54) METAL COMPLEXES

(75) Inventors: Philipp Stoessel, Frankfurt am Main (DE); Esther Breuning, Ober-Ramstadt (DE)

(73) Assignee: Merck Patent GmbH (DE)

( * ) Notice: Subject to any disclaimer, the term of this patent is extended or adjusted under 35 U.S.C. 154(b) by 846 days.

(21) Appl. No.: 14/237,462

(22) PCT Filed: Jul. 17, 2012

(86) PCT No.: PCT/EP2012/002991
§ 371 (c)(1),
(2), (4) Date: Feb. 6, 2014

(87) PCT Pub. No.: WO2013/020631
PCT Pub. Date: Feb. 14, 2013

(65) Prior Publication Data
US 2014/0183422 A1   Jul. 3, 2014

(30) Foreign Application Priority Data
Aug. 10, 2011  (EP) .................................. 11006562

(51) Int. Cl.
H01L 51/54     (2006.01)
C09K 11/06     (2006.01)
H01L 51/00     (2006.01)
C07F 15/00     (2006.01)
H01L 51/50     (2006.01)

(52) U.S. Cl.
CPC ...... *H01L 51/0087* (2013.01); *C07F 15/0086* (2013.01); *C09K 11/06* (2013.01); *H01L 51/009* (2013.01); *H01L 51/0084* (2013.01); *H01L 51/0085* (2013.01); *C09K 2211/1029* (2013.01); *C09K 2211/185* (2013.01); *H01L 51/0067* (2013.01); *H01L 51/0072* (2013.01); *H01L 51/5016* (2013.01); *H01L 2251/5384* (2013.01); *Y02E 10/549* (2013.01)

(58) Field of Classification Search
None
See application file for complete search history.

(56) References Cited

U.S. PATENT DOCUMENTS

| 8,153,278 | B2 | 4/2012 | Kinoshita et al. | |
|---|---|---|---|---|
| 8,216,698 | B2 | 7/2012 | Murakami et al. | |
| 2006/0202197 | A1* | 9/2006 | Nakayama et al. | C07F 15/0086 257/40 |
| 2006/0286406 | A1 | 12/2006 | Igarashi et al. | |
| 2008/0161567 | A1 | 7/2008 | Stoessel et al. | |
| 2008/0200677 | A1 | 8/2008 | Stoessel et al. | |
| 2009/0153045 | A1 | 6/2009 | Kinoshita et al. | |
| 2009/0261721 | A1* | 10/2009 | Murakami et al. | C09K 11/06 313/504 |
| 2011/0049496 | A1 | 3/2011 | Fukuzaki | |
| 2012/0187349 | A1 | 7/2012 | Stoessel et al. | |

FOREIGN PATENT DOCUMENTS

| EP | 2360752 A1 | 8/2011 |
|---|---|---|
| JP | 2009-266943 A | 11/2009 |
| JP | 2009-272339 A | 11/2009 |
| JP | 2009-283891 A | 12/2009 |
| JP | 2009-283913 A | 12/2009 |
| JP | 2011-112631 A | 6/2011 |
| TW | 200701837 A | 1/2007 |
| TW | 201026817 A | 7/2010 |
| WO | WO-2006081973 A1 | 8/2006 |
| WO | WO-2007006380 A1 | 1/2007 |
| WO | WO-2011035836 A1 | 3/2011 |

OTHER PUBLICATIONS

Chinese Office Action dated Mar. 24, 2015 for Chinese Application No. 201280039105.7.
Japanese Office Action dated Mar. 15, 2616 for Japanese Application No. 2014-524287.
International Search Report for PCT/EP2012/002991 dated Oct. 18, 2012.

* cited by examiner

*Primary Examiner* — Marie R. Yamnitzky
(74) *Attorney, Agent, or Firm* — Drinker Biddle & Reath LLP

(57) ABSTRACT

The present invention relates to metal complexes of formula (1),

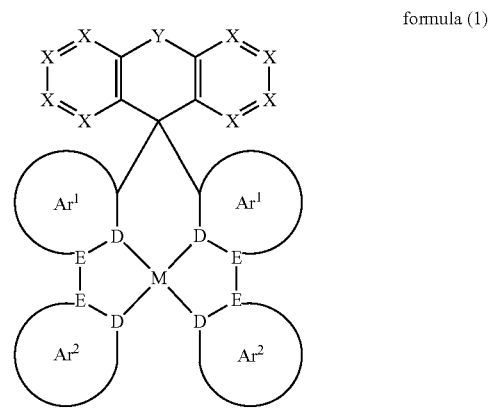

formula (1)

and to electronic devices, in particular organic electroluminescent devices, comprising these metal complexes, in particular as emitters.

20 Claims, No Drawings

METAL COMPLEXES

CROSS-REFERENCE TO RELATED APPLICATIONS

This application is a national stage application (under 35 U.S.C. §371) of PCT/EP2012/002991, filed Jul. 17, 2012, which claims benefit of European application 11006562.0, filed Aug. 10, 2011.

The present invention relates to metal complexes which are suitable for use in organic electroluminescent devices, in particular as emitters.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed are frequently organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement in the case of OLEDs which exhibit triplet emission, in particular with respect to efficiency, operating voltage and lifetime.

In accordance with the prior art, the triplet emitters employed in phosphorescent OLEDs are, in particular, iridium or platinum complexes. An improvement in the platinum complexes used can be achieved by employing metal complexes having tetradentate ligands, as a result of which the complexes have higher thermal stability (WO 2004/108857, WO 2005/042550, WO 2005/042444). In these complexes, two bidentate part-ligands are connected to one another by a bridging group, called bridgehead below. In accordance with the prior art, platinum complexes having tetradentate ligands are also known (WO 2010/069442) which contain a fluorene as bridgehead, where the two bidentate part-ligands are each bonded at the 9-position of the fluorene. These complexes generally have good efficiency and a good lifetime, but there is still a need for improvement here, in particular in the case of the lifetime.

The object of the present invention is therefore the provision of novel metal complexes which have improvements here and are suitable as emitters for use in OLEDs.

Surprisingly, it has been found that the metal chelate complexes described in greater detail below achieve this object and result in improvements in the organic electroluminescent device. The present invention therefore relates to these metal complexes and to organic electroluminescent devices which comprise these complexes.

The invention relates to a compound of the formula (1),

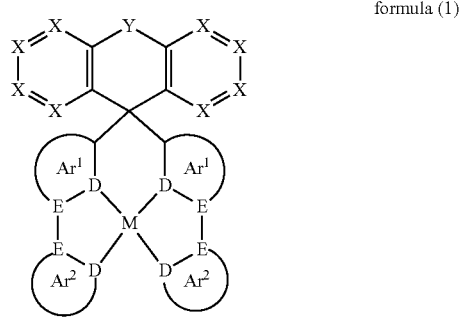

formula (1)

where the following applies to the symbols used:

M is selected on each occurrence, identically or differently, from the group consisting of platinum, palladium, nickel, rhodium, iridium and gold;

X is on each occurrence, identically or differently, $CR^1$ or N;

Y is $CR_2$, C=O, BR, $SiR_2$, NR, PR, P(=O)R, O, S, CR=CR, $CR_2$—$CR_2$ or CR=N;

or Y stands for a group of the following formula (2),

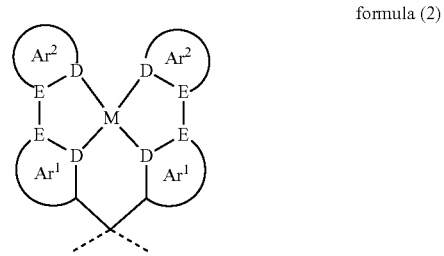

formula (2)

where the dashed bonds indicates the linking of this group;

D is on each occurrence, identically or differently, C or N;

E is C if the ring in which this E is bonded is an aromatic or heteroaromatic six-membered ring; or is C or N if the ring in which this E is bonded is a heteroaromatic five-membered ring;

$Ar^1$ is on each occurrence, identically or differently, together with the groups D and E, an aryl or heteroaryl group having 5 to 18 aromatic ring atoms, which may be substituted by one or more radicals $R^1$; adjacent groups $Ar^1$ and $Ar^2$ here may also be linked to one another by two radicals $R^1$, which are linked to one another, or by a group $CR^2$=N;

$Ar^2$ is on each occurrence, identically or differently, together with the groups D and E, an aryl or heteroaryl group having 5 to 18 aromatic ring atoms, which may be substituted by one or more radicals $R^1$; adjacent groups $Ar^2$ and $Ar^1$ here may also be linked to one another by two radicals $R^1$, which are linked to one another, or by a group $CR^2$=N;

R is on each occurrence, identically or differently, H, D, F, $N(R^2)_2$, CN, C(=O)$N(R^2)_2$, $Si(R^2)_3$, $B(OR^2)_2$, C(=O)$R^2$, P(=O)$(R^2)_2$, S(=O)$R^2$, $S(=O)_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^2$, where one or more non-adjacent $CH_2$ groups may be replaced by $R^2C$=$CR^2$, C=C, $Si(R^2)_2$, C=O, $NR^2$, O, S or $CONR^2$ and where one or more H atoms may be replaced by D, F, Cl, Br, I or CN, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$; two radicals R here which are bonded to the same C or Si atom may also form a mono- or polycyclic, aliphatic or aromatic ring system with one another;

$R^1$ is on each occurrence, identically or differently, H, D, F, Cl, Br, I, $N(R^2)_2$, CN, $NO_2$, OH, COOH, C(=O)$N(R^2)_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals R$^2$, where one or more non-adjacent CH$_2$ groups may be replaced by R$^2$C=CR$^2$, C≡C, Si(R$^2$)$_2$, C=O, NR$^2$, O, S or CONR$^2$ and where one or more H atoms may be replaced by D, F, Cl, Br, I or CN, or an aromatic or heteroaromatic ring system having 5 to 60 aromatic ring atoms, which may in each case be substituted by one or more radicals R$^2$, or an aryloxy or heteroaryloxy group having 5 to 40 aromatic ring atoms, which may be substituted by one or more radicals R$^2$, or an aralkyl or heteroaralkyl group having 5 to 40 aromatic ring atoms, which may be substituted by one or more radicals R$^2$; two adjacent radicals R$^1$ here may also form a mono- or polycyclic, aliphatic or aromatic ring system with one another; furthermore, the radicals R$^1$ which are bonded to adjacent groups Ar$^1$ and Ar$^2$ may also form a mono- or polycyclic, aliphatic or aromatic ring system with one another; furthermore, two groups R$^1$ which are bonded to the two groups Ar$^2$ may also form a ring system with one another and thus build up a cyclic ligand;

R$^2$ is on each occurrence, identically or differently, H, D, F, Cl, Br, I, N(R$^3$)$_2$, CN, NO$_2$, Si(R$^3$)$_3$, B(OR$^3$)$_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals R$^3$, where one or more non-adjacent CH$_2$ groups may be replaced by R$^3$C=CR$^3$, C≡C, Si(R$^3$)$_2$, C=O, NR$^3$, O, S or CONR$^3$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy or heteroaryloxy group having 5 to 40 aromatic ring atoms, which may be substituted by one or more radicals R$^3$, or an aralkyl or heteroaralkyl group having 5 to 40 aromatic ring atoms, which may be substituted by one or more radicals R$^3$; two or more adjacent radicals R$^3$ here may form a mono- or polycyclic, aliphatic ring system with one another;

R$^3$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R$^3$ here may also form a mono- or polycyclic, aliphatic ring system with one another;

two groups Ar$^2$ here may also be bridged to one another by a group Y.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a C$_1$- to C$_{40}$-alkyl group, in which, in addition, individual H atoms or CH$_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A C$_1$- to C$_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, cis- or trans-indenocarbazole, cis- or trans-indolocarbazole, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

As stated above, radicals R which are bonded to the same C or Si atom, or adjacent radicals $R^1$ or radicals $R^1$ on adjacent groups $Ar^1$ and $Ar^2$ may also form a ring system with one another. Adjacent radicals in the sense of the present invention are taken to mean radicals which are bonded to atoms which are bonded directly to one another. Adjacent groups $Ar^1$ and $Ar^2$ are taken to mean groups $Ar^1$ and $Ar^2$ which are bonded directly to one another. The radicals here are as defined above, and two radicals are bonded to one another, in each case with formal elimination of a hydrogen atom with formation of a chemical bond. If the radicals are alkyl groups, the formation of a condensed-on cycloalkyl group, for example, is thus possible. If the radicals are vinyl groups or a vinyl group and a hydrogen atom, the formation of a condensed aryl group, for example, is thus possible. If the radicals R or $R^1$ form a ring system, this is then preferably a five-membered ring or a six-membered ring. If two radicals R form a ring system with one another, a spiro system thereby arises.

The ring formation is illustrated again by the following scheme:

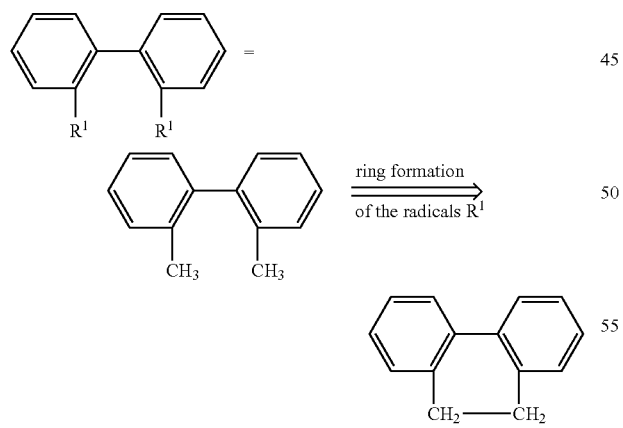

Furthermore, however, the above-mentioned formulation is also intended to be taken to mean that, in the case where one of the two radicals represents hydrogen, the second radical is bonded at the position at which the hydrogen atom was bonded, with formation of a ring. This is illustrated by the following scheme:

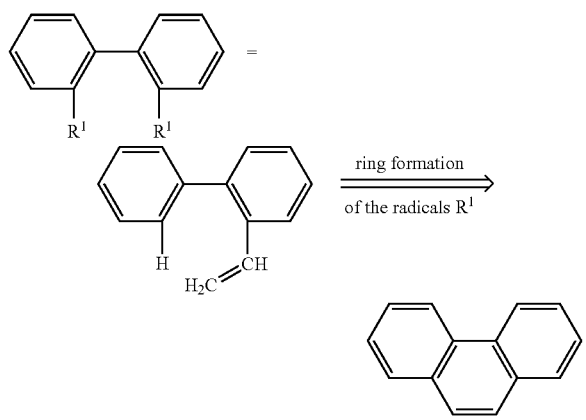

Preference is given to compounds of the formula (1), characterised in that these are uncharged, i.e. are electrically neutral. This is achieved in a simple manner by the charge of the ligand being selected so that it compensates for the charge of the complexed metal atom M. The charge of the ligand arises from the number of coordinating carbon or nitrogen atoms, each of which have a negative charge.

Preference is furthermore given to compounds of the formula (1), characterised in that the sum of the valence electrons around the metal atom is 16.

The metal is preferably selected from the above-mentioned metals in the oxidation states Pt(II), Pd(II), Ni(II), Rh(I), Ir(I) and Au(III). Particular preference is given to Pt(II), Ir(I) and Au(III). Very particular preference is given to Pt(II).

Furthermore preferably, two groups D in the compound according to the invention stand for N, and the other two groups D stand for C.

Preferred structures of the formula (1) are therefore the structures of the following formulae (3), (4), (5) or (6), formula (3)

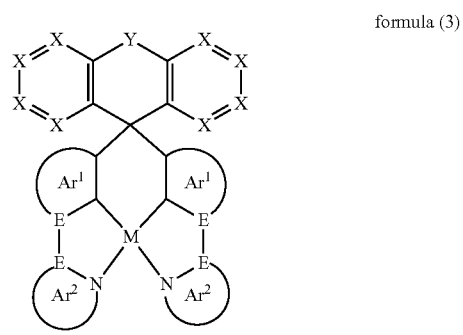

formula (4)

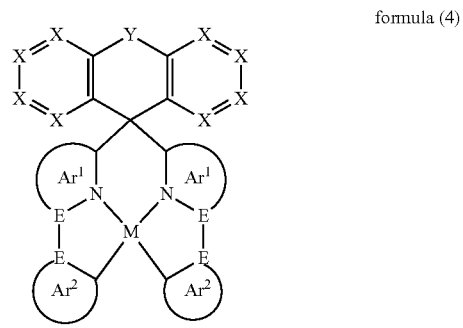

formula (5)

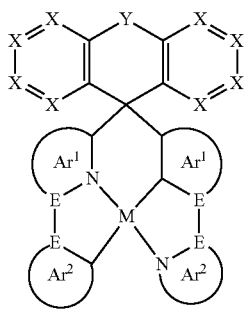

formula (6)

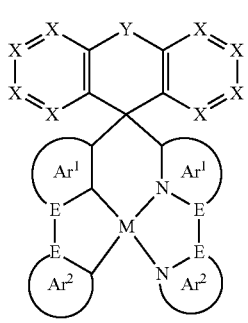

where the symbols used have the meanings given above. The structures of the formula (3) and (4) are particularly preferred here.

Furthermore preferably, Y stands for $CR_2$, NR, O, S or for a structure of the formula (2), particularly preferably for $CR_2$, NR or O, very particularly preferably for O. If Y stands for a structure of the formula (2), the two platinum-containing halves of the compound are electronically decoupled.

Furthermore preferably, a maximum of two symbols X per ring in formula (1), (3), (4), (5) and (6) stand for N and the other symbols X stand for $CR^1$. Particularly preferably, a maximum of one symbol X per ring stands for N, and very particularly preferably all symbols X stand for $CR^1$.

Particularly preferred embodiments are therefore the structures of the formulae (3a), (4a), (5a) and (6a), formula (3a)

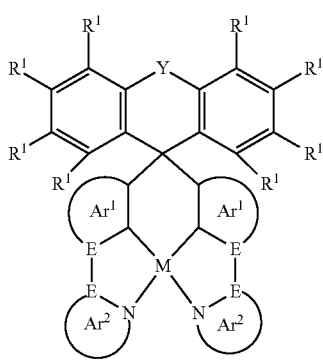

formula (4a)

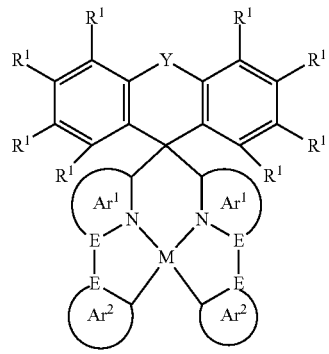

formula (5a)

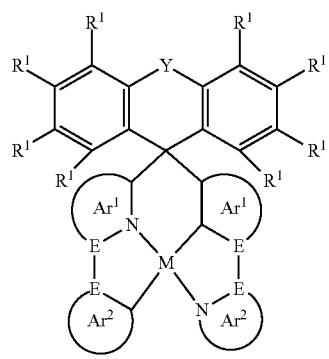

formula (6a)

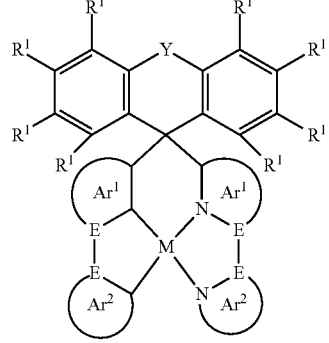

where the symbols used have the meanings given above and the radicals $R^1$ explicitly drawn in preferably stand for H.

Again furthermore preferably, E in the above-mentioned formulae stands for C.

Furthermore preferably, all groups $Ar^1$ are selected identically and are also identically substituted. Likewise preferably, all groups $Ar^2$ are selected identically and are also identically substituted. These are thus preferably symmetrical ligands of the formula (3) or (4) or (3a) or (4a) respectively having two identical part-ligands.

In a preferred embodiment of the invention, $Ar^1$ and $Ar^2$ have 5 to 13 aromatic ring atoms, particularly preferably 5 to 10 aromatic ring atoms, and may be substituted by one or more radicals $R^1$.

The part-ligands $Ar^1$-$Ar^2$ are preferably each bidentate monoanionic ligands, as are generally used in the area of phosphorescent metal complexes for organic electroluminescent devices. Suitable as group $Ar^1$ is preferably in each case one of the following groups (7) to (26) and suitable as group $Ar^2$ is preferably in each case one of the following groups (27) to (48). The groups here are preferably selected in such a way that one of the groups $Ar^1$ or $Ar^2$ in the part-ligand Ar¹-Ar² is bonded via a neutral nitrogen atom or a carbene carbon atom and the other of the groups Ar¹ or Ar² in the part-ligand Ar¹-Ar² is bonded via a negatively charged carbon atom or a negatively charged nitrogen atom.

Suitable structures Ar¹ are thus the structures of the following formulae (7) to (26h),

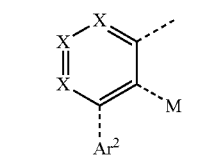

formula (7)

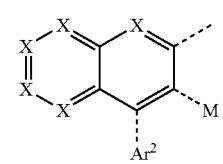

formula (8)

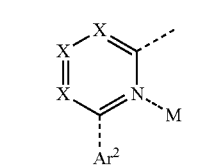

formula (9)

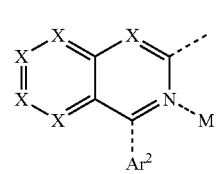

formula (10)

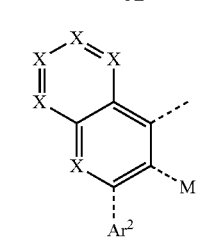

formula (11)

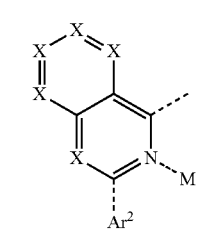

formula (12)

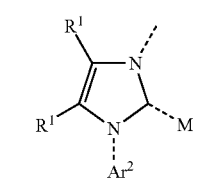

formula (13)

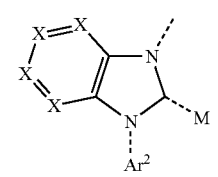

formula (14)

-continued

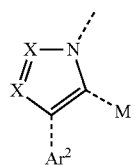

formula (15)

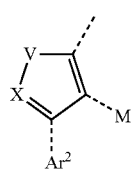

formula (16)

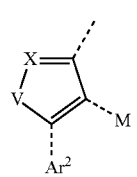

formula (17)

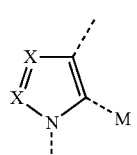

formula (18)

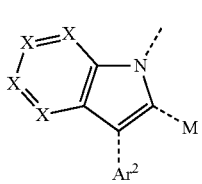

formula (19)

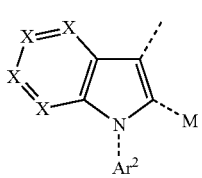

formula (20)

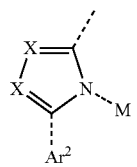

formula (21)

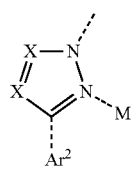

formula (22)

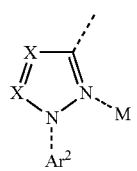

formula (23)

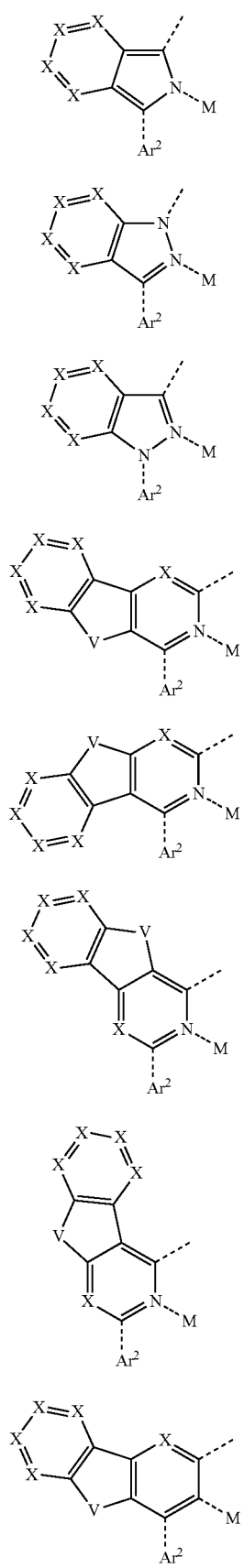
formula (24)
formula (25)
formula (26)
formula (26a)
formula (26b)
formula (26c)
formula (26d)
formula (26e)
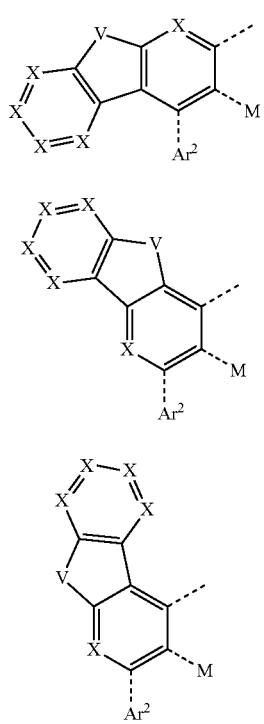
formula (26f)
formula (26g)
formula (26h)
Suitable structures $Ar^2$ are the structures of the following formulae (27) to (48d),
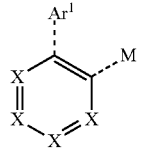
formula (27)
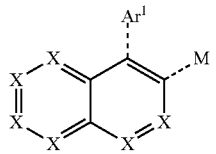
formula (28)
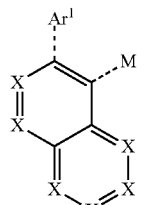
formula (29)
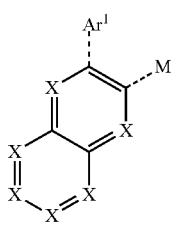
formula (30)

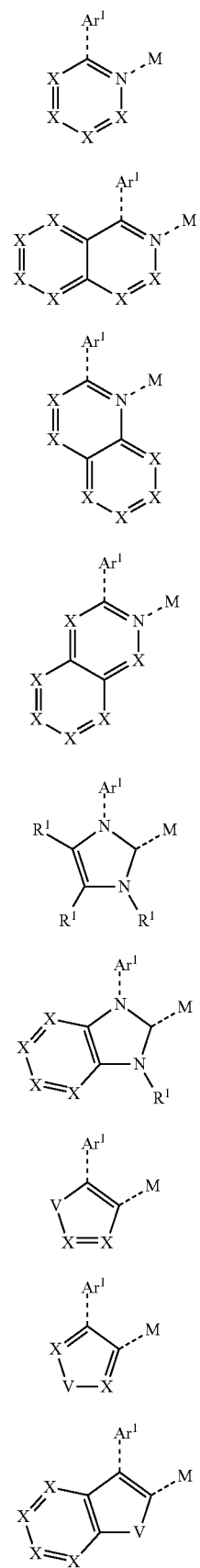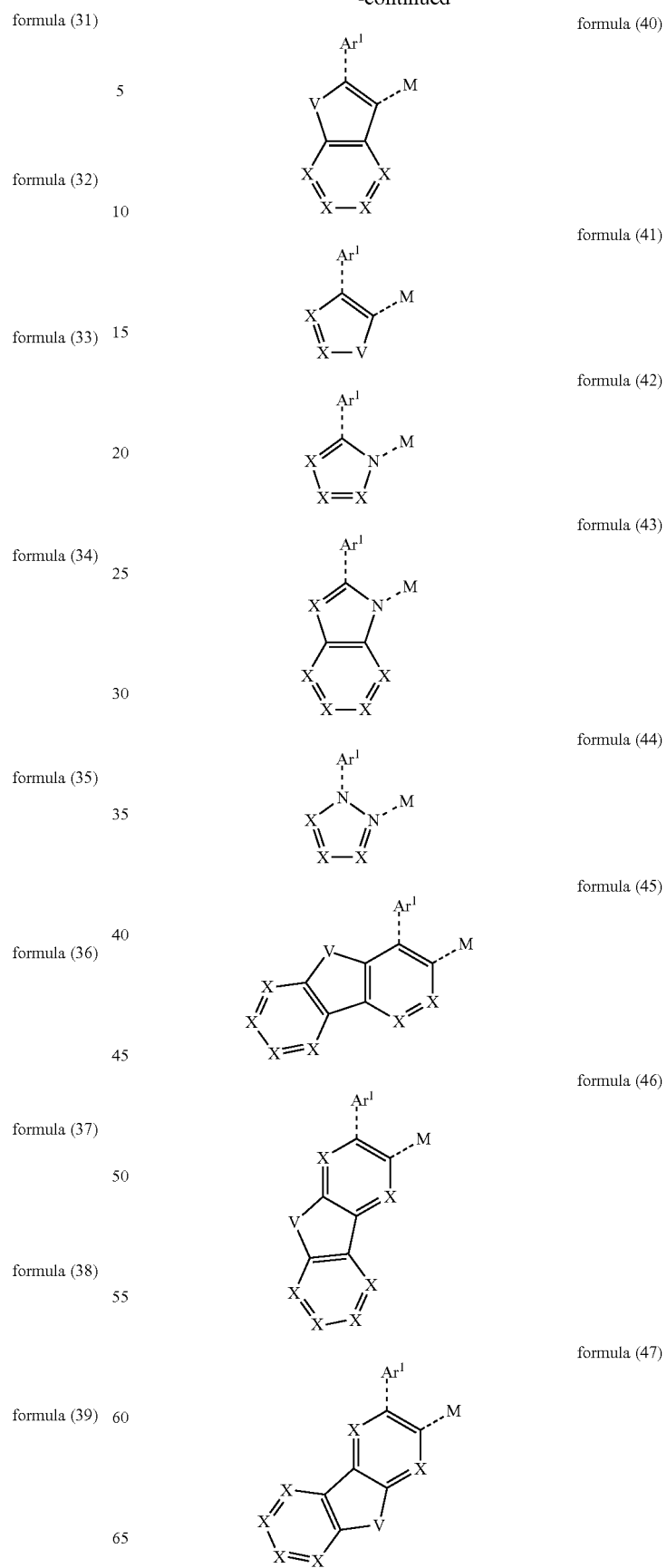

-continued

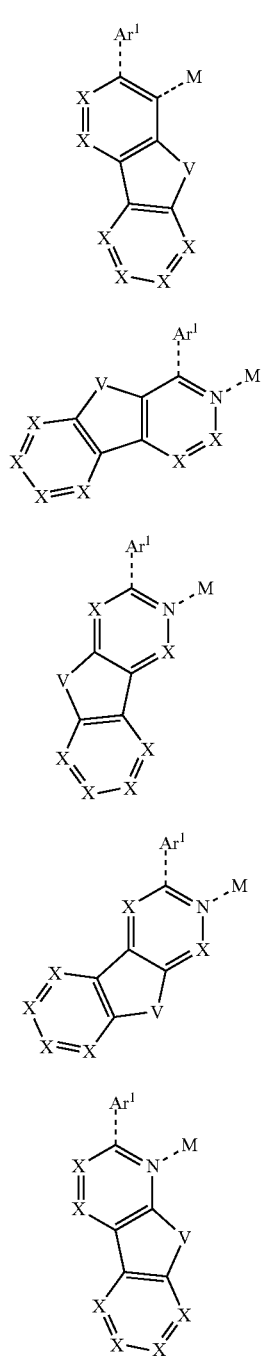

formula (48)

formula (48a)

formula (48b)

formula (48c)

formula (48d)

In the structures of the formulae (7) to (48), the bond to the carbon atom of the bridgehead, to M and to Ar¹ or to Ar² is in each case indicated by dashed bonds. Furthermore, X and R¹ in the formulae (7) to (48) have the same meaning as described above and V stands on each occurrence, identically or differently, for O, S, NR¹ or C(R¹)$_2$. Preferably a maximum of two symbols X in each group stand for N, particularly preferably a maximum of one symbol X in each group stands for N. Very particularly preferably all symbols X stand for CR¹.

Particularly preferred groups Ar¹ are the groups of the formulae (7), (8), (9), (10), (13) and (14). Particularly preferred groups Ar² are the groups of the formulae (27), (28), (30), (31), (32), (34), (35), (36), (39), (40), (43), (44), (46), (47) and (48).

Particular preference is therefore given to the following combinations of Ar¹ and Ar²:

| Ar¹ | Ar² |
|---|---|
| Formula (7) | Formula (27) |
| Formula (7) | Formula (28) |
| Formula (7) | Formula (30) |
| Formula (7) | Formula (31) |
| Formula (7) | Formula (32) |
| Formula (7) | Formula (34) |
| Formula (7) | Formula (35) |
| Formula (7) | Formula (36) |
| Formula (7) | Formula (39) |
| Formula (7) | Formula (40) |
| Formula (7) | Formula (43) |
| Formula (7) | Formula (44) |
| Formula (7) | Formula (46) |
| Formula (7) | Formula (47) |
| Formula (7) | Formula (48) |
| Formula (8) | Formula (27) |
| Formula (8) | Formula (28) |
| Formula (8) | Formula (30) |
| Formula (8) | Formula (31) |
| Formula (8) | Formula (32) |
| Formula (8) | Formula (34) |
| Formula (8) | Formula (35) |
| Formula (8) | Formula (36) |
| Formula (8) | Formula (39) |
| Formula (8) | Formula (40) |
| Formula (8) | Formula (43) |
| Formula (8) | Formula (44) |
| Formula (8) | Formula (46) |
| Formula (8) | Formula (47) |
| Formula (8) | Formula (48) |
| Formula (9) | Formula (27) |
| Formula (9) | Formula (28) |
| Formula (9) | Formula (30) |
| Formula (9) | Formula (31) |
| Formula (9) | Formula (32) |
| Formula (9) | Formula (34) |
| Formula (9) | Formula (35) |
| Formula (9) | Formula (36) |
| Formula (9) | Formula (39) |
| Formula (9) | Formula (40) |
| Formula (9) | Formula (43) |
| Formula (9) | Formula (44) |
| Formula (9) | Formula (46) |
| Formula (9) | Formula (47) |
| Formula (9) | Formula (48) |
| Formula (10) | Formula (27) |
| Formula (10) | Formula (28) |
| Formula (10) | Formula (30) |
| Formula (10) | Formula (31) |
| Formula (10) | Formula (32) |
| Formula (10) | Formula (34) |
| Formula (10) | Formula (35) |
| Formula (10) | Formula (36) |
| Formula (10) | Formula (39) |
| Formula (10) | Formula (40) |
| Formula (10) | Formula (43) |
| Formula (10) | Formula (44) |
| Formula (10) | Formula (46) |
| Formula (10) | Formula (47) |
| Formula (10) | Formula (48) |
| Formula (13) | Formula (27) |
| Formula (13) | Formula (28) |
| Formula (13) | Formula (30) |
| Formula (13) | Formula (31) |
| Formula (13) | Formula (32) |
| Formula (13) | Formula (34) |
| Formula (13) | Formula (35) |
| Formula (13) | Formula (36) |
| Formula (13) | Formula (39) |
| Formula (13) | Formula (40) |
| Formula (13) | Formula (43) |
| Formula (13) | Formula (44) |

| Ar¹ | Ar² |
|---|---|
| Formula (13) | Formula (46) |
| Formula (13) | Formula (47) |
| Formula (13) | Formula (48) |
| Formula (14) | Formula (27) |
| Formula (14) | Formula (28) |
| Formula (14) | Formula (30) |
| Formula (14) | Formula (31) |
| Formula (14) | Formula (32) |
| Formula (14) | Formula (34) |
| Formula (14) | Formula (35) |
| Formula (14) | Formula (36) |
| Formula (14) | Formula (39) |
| Formula (14) | Formula (40) |
| Formula (14) | Formula (43) |
| Formula (14) | Formula (44) |
| Formula (14) | Formula (46) |
| Formula (14) | Formula (47) |
| Formula (14) | Formula (48) |

As indicated above, two radicals on adjacent groups Ar¹ and Ar² may also form a ring with one another. A ring closure of this type preferably takes place via a group $CR^2=CR^2$, $CR^2=N$, $C(R^2)_2-C(R^2)_2$, $C(=O)-O$ or $C(=O)-NR^2$, where $CR^2=CR^2$ and $CR^2=N$ are preferred. In total one condensed aryl or heteroaryl group can thereby also be formed, so that Ar¹ and Ar² no longer represent separate aryl groups.

Preferred groups Ar¹-Ar² which are formed by a ring-closure reaction of this type are the groups of the following formulae (49) to (59),

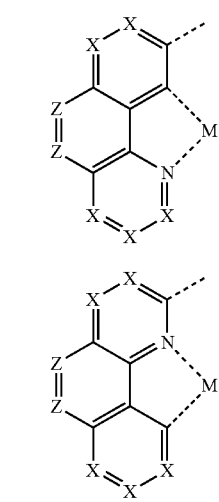

formula (49)

formula (50)

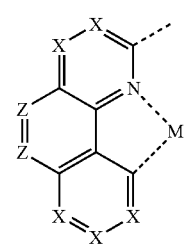

formula (51)

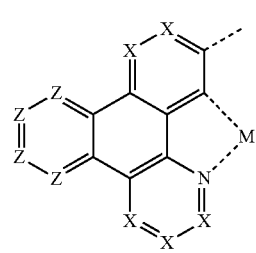

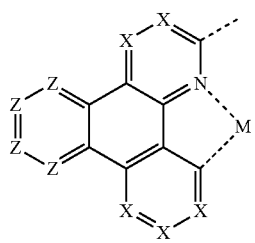

formula (52)

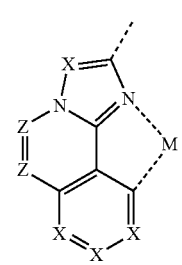

formula (53)

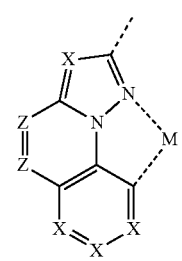

formula (54)

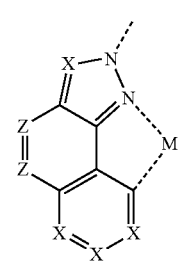

formula (55)

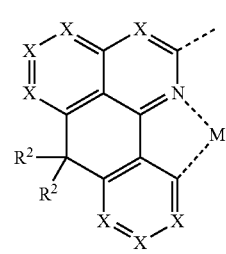

formula (56)

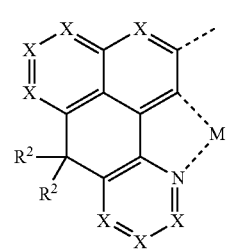

formula (57)

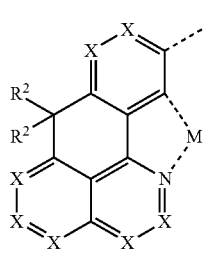

formula (58)

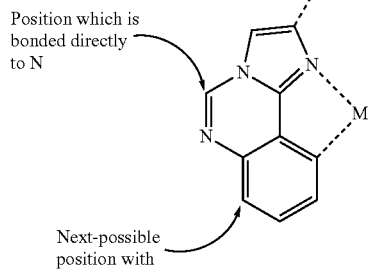

Position which is bonded directly to N

Next-possible position with

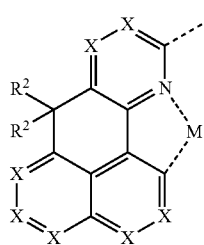

formula (59)

where the bond to the metal or to the bridgehead carbon atom are in each case indicated by dashed bonds, Z stands on each occurrence, identically or differently, for $CR^2$ or N, where a maximum of one group Z stands for N, and the other symbols have the meanings given above.

Preferred radicals $R^1$ on $Ar^1$ or $Ar^2$ or on the aromatic groups of the bridgehead are selected on each occurrence, identically or differently, from the group consisting of H, D, F, $N(R^2)_2$, CN, C($=$O)$R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$.

These radicals $R^1$ are particularly preferably selected on each occurrence, identically or differently, from the group consisting of H, D, F, $N(R^2)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$.

It is furthermore preferred, if a group X in the formulae (7) to (59) stands for N, for the group X or Z which is adjacent to this nitrogen atom to stand for $CR^1$ (in the case of a group X) or for $CR^2$ (in the case of a group Z) and for $R^1$ or $R^2$ not to be equal to H or D and preferably for an alkyl group having 1 to 10 C atoms or an aromatic ring system having 5 to 30 aromatic ring atoms. The alkyl group here is preferably a secondary or tertiary alkyl group having 3 to 10 C atoms, particularly preferably having 3 to 5 C atoms.

"Adjacent" here means that this X or Z can be bonded directly to the nitrogen or that it is the next-possible position in which an X is present. This is explained again with reference to a specific ligand in the following diagrammatic representation:

In this representation, both the position which is bonded directly to the nitrogen and also the next-possible position in which an X is present are marked. Both positions are regarded as adjacent positions to the nitrogen atom in the sense of the present application.

It is furthermore preferred, if a group Z in the formulae (49) to (55) stands for N, for the group X or Z which is adjacent to this nitrogen atom to stand for $CR^1$ (in the case of a group X) or for $CR^2$ (in the case of a group Z) and for $R^1$ or $R^2$ not to be equal to H or D and preferably for an alkyl group having 1 to 10 C atoms or an aromatic ring system having 5 to 30 aromatic ring atoms. The alkyl group here is preferably a secondary or tertiary alkyl group having 3 to 10 C atoms, particularly preferably having 3 to 5 C atoms.

If the group Y stands for a group $CR_2$ or $SiR_2$, the group R then preferably stands, identically or differently on each occurrence, for a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$ and which preferably contains no condensed aryl or heteroaryl groups; two or more radicals R which are bonded to the same carbon or silicon atom here may also form a mono- or polycyclic, aliphatic or aromatic ring system with one another. Particularly preferred radicals R are selected on each occurrence, identically or differently, from the group consisting of H, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms which contains no condensed aryl or heteroaryl groups and which may in each case be substituted by one or more radicals $R^2$; two radicals R which are bonded to the same carbon or silicon atom here may also form a mono- or polycyclic, aliphatic or aromatic ring system with one another.

If the radicals R which are bonded to the same carbon or silicon atom form a ring system with one another, this is, in a preferred embodiment of the invention, a structure of the following formula (a), formula (b) or formula (c),

formula (a)

-continued formula (b)

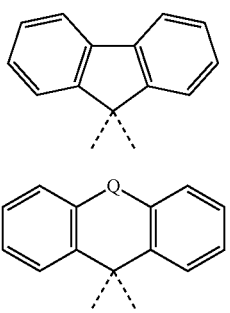

formula (c)

where Q stands for $C(R^2)_2$, $NR^2$, O or S, the structures may also be substituted by one or more radicals $R^2$ and m stands for 1, 2, 3, 4 or 5, preferably for 3 or 4. The bonds shown in dashed form here stand for the bond from this group Y to the bridgehead. The phenyl groups in the formulae (b) and (c) are preferably unsubstituted.

If the group Y stands for a group NR, BR, PR or P(=O)R, the group R then preferably stands for an aromatic or heteroaromatic ring system having 5 to 18 aromatic ring atoms, which may in each case be substituted by one or more radicals $R^2$ and which preferably contains no condensed aryl or heteroaryl groups. Particularly preferred aromatic or heteroaromatic ring systems are selected from ortho-, meta- or para-biphenyl, terphenyl, quaterphenyl, 2,4,6-trialkylphenyl, in particular mesityl, or 2,6-dialkylphenyl, in particular 2,6-dimethylphenyl.

If Y stands for a group of the formula (2), the two metal complexes which are linked to one another via the bridgehead are then preferably identical and are also identically substituted.

The above-mentioned preferred embodiments can be combined with one another as desired. In a particularly preferred embodiment of the invention, the above-mentioned preferred embodiments apply simultaneously.

In a preferred embodiment of the invention, the compounds of the formula (1) or (3) to (6) or (3a) to (6a) are therefore uncharged, and the following applies:

M is selected from the group consisting of Pt(II), Pd(II), Ni(II), Rh(I), Ir(I) and Au(III);

Y is selected from the group consisting of $CR_2$, C=O, NR, O and S;

X is, identically or differently on each occurrence, $CR^1$ or N, where a maximum of two symbols X per ring for N and the other symbols X stand for $CR^1$;

$Ar^1$ is selected, identically or differently on each occurrence, from the structures of the above-mentioned formulae (7) to (26);

$Ar^2$ is selected, identically or differently on each occurrence, from the structures of the above-mentioned formulae (27) to (48);

or $Ar^1$-$Ar^2$ is selected, identically or differently on each occurrence, from the structures of the above-mentioned formulae (49) to (59);

$R^1$ is selected on each occurrence, identically or differently, from the group consisting of H, D, F, $N(R^2)_2$, CN, C(=O)$R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$;

R stands, for Y=$CR_2$, identically or differently on each occurrence, for a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$ and which preferably contains no condensed aryl or heteroaryl groups; two or more radicals R which are bonded to the same carbon or silicon atom here may also form a mono- or polycyclic, aliphatic or aromatic ring system with one another, resulting in the formation of a spiro system;

and stands, for Y=NR, for an aromatic or heteroaromatic ring system having 5 to 18 aromatic ring atoms, which may in each case be substituted by one or more radicals $R^2$ and which preferably contains no condensed aryl or heteroaryl groups.

In a particularly preferred embodiment of the invention, the compounds of the formula (1) or (3) to (6) or (3a) to (6a) are therefore uncharged, and the following applies:

M is selected from the group consisting of Pt(II), Ir(I) and Au(III), in particular Pt(II);

Y is selected from the group consisting of $CR_2$, NR and S;

X is, identically or differently on each occurrence, $CR^1$ or N, where a maximum of one symbol X per ring stands for N and the other symbols X stand for $CR^1$ and preferably all symbols X stand for $CR^1$.

$Ar^1$ is selected, identically or differently on each occurrence, from the structures of the above-mentioned formulae (7), (8), (9), (10), (13) and (14);

$Ar^2$ is selected, identically or differently on each occurrence, from the structures of the above-mentioned formulae (27), (28), (30), (31), (32), (34), (35), (36), (39), (40), (43), (44), (46) and (47);

or $Ar^1$-$Ar^2$ is selected, identically or differently on each occurrence, from the structures of the above-mentioned formulae (49) to (59);

$R^1$ is selected on each occurrence, identically or differently, from the group consisting of H, D, F, $N(R^2)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^2$;

R stands, for Y=$CR_2$, identically or differently on each occurrence, for a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which contains no condensed aryl or heteroaryl groups and which may in each case be substituted by one or more radicals $R^2$; two radicals R which are bonded to the same carbon or silicon atom here may also form a mono- or polycyclic, aliphatic or aromatic ring system with one another, resulting in the formation of a spiro system;

and stands, for Y=NR, for an aromatic or heteroaromatic ring system having 5 to 18 aromatic ring atoms, which may in each case be substituted by one or more radicals $R^2$ and which contains no condensed aryl or heteroaryl groups.

The ligands of the compounds according to the invention can be prepared in accordance with Scheme 1. Ortho-halogen-functionalised pyridine ketones are reacted with organometallic compounds to give the corresponding triarylmethanols, which are then cyclised in a second step with acid catalysis to give the corresponding spiro compounds. A subsequent Ullmann or Suzuki coupling gives the ligands, which can be reacted with suitable metal precursors to give the metal complexes according to the invention. The synthesis of the platinum complexes is depicted by way of example in the following schemes.

Ketones which already carry the two part-ligands can also be reacted analogously with organometallic compounds to give the corresponding triarylmethanols, which are then cyclised in a second step with acid catalysis to give the corresponding spiro compounds, as shown by way of example for phenanthridine derivatives in Scheme 2. The ketones used for this purpose can be prepared by methods familiar to the person skilled in the art, for example from arylheteroaryl halides and C1 electrophiles. Asymmetrical metal complexes are accessible from asymmetrical ketones by this route.

Scheme 1:

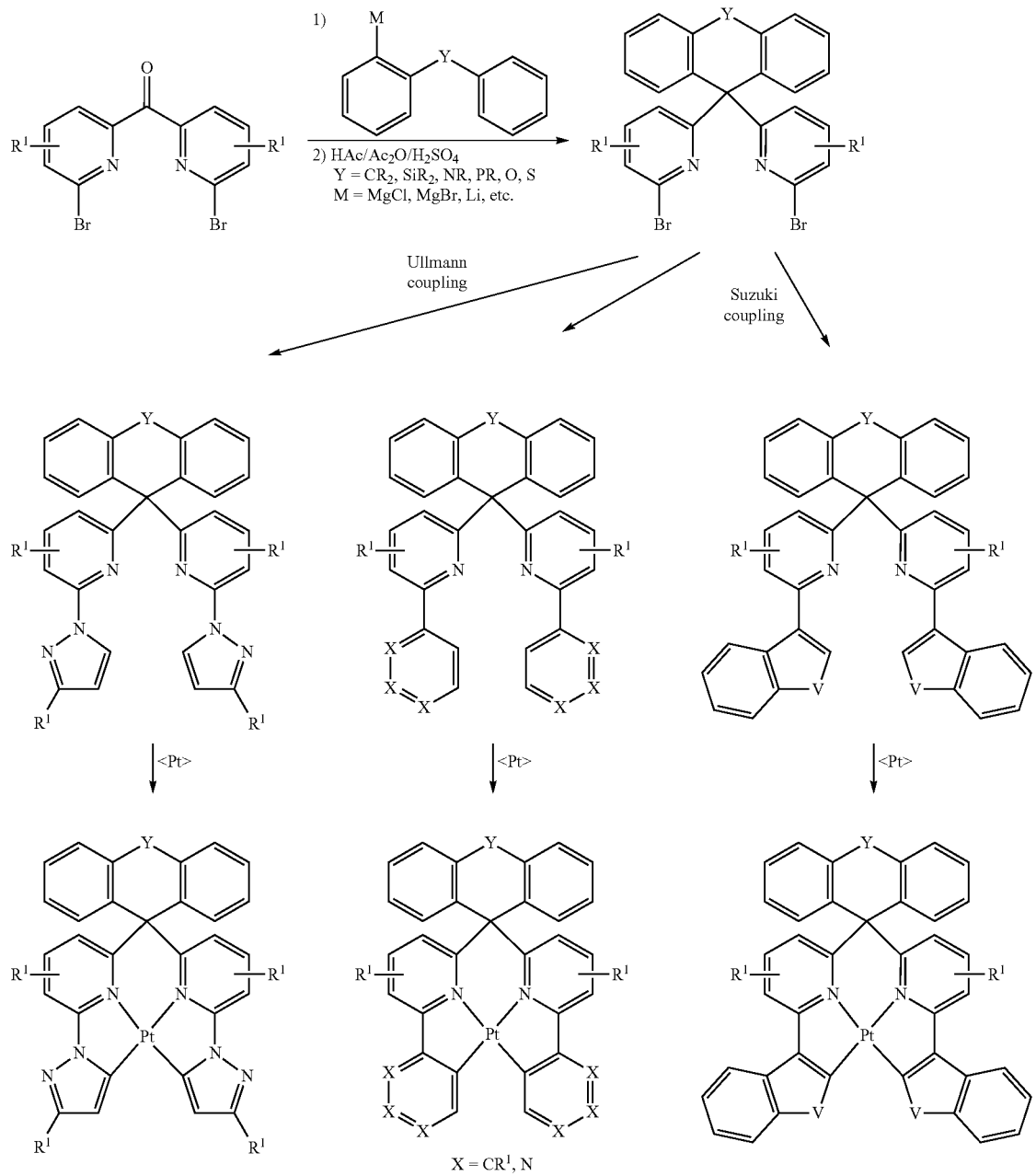

Scheme 2:
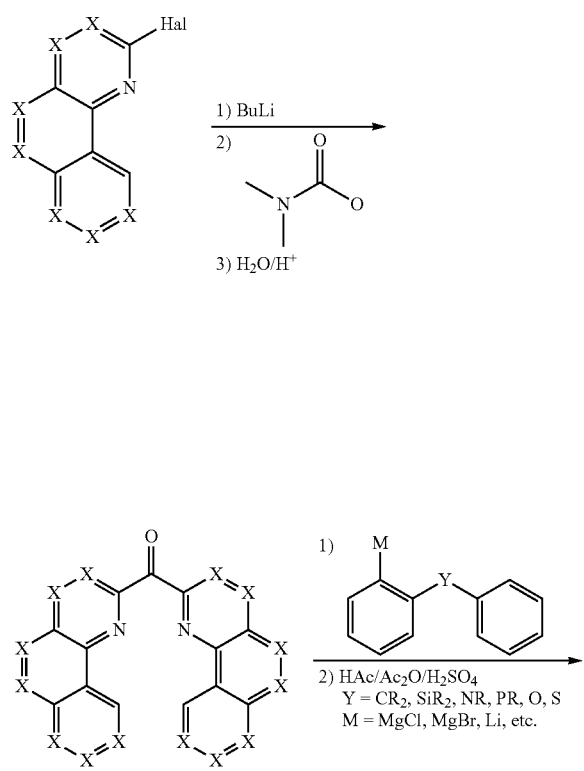
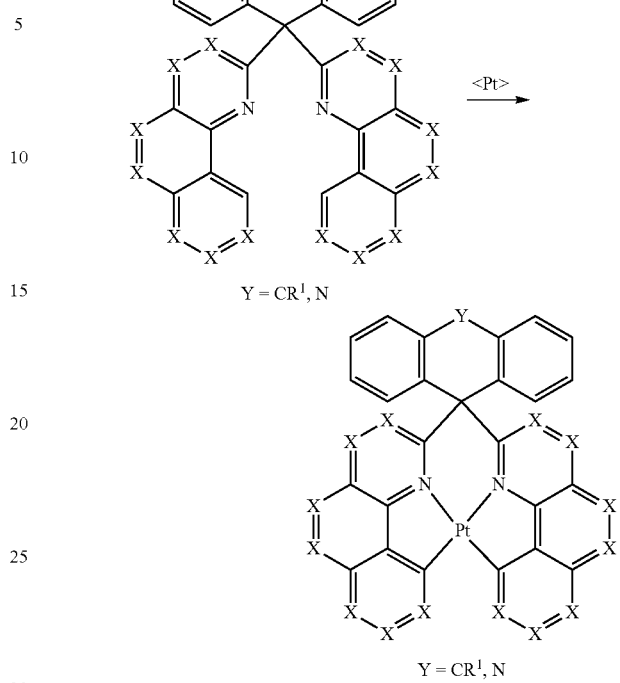
Starting from 3,3'-diaryl ketones, metal complexes which carry the spirobridging C atom on the o-metallated aromatic ring are accessible in accordance with Scheme 3.
Scheme 3:
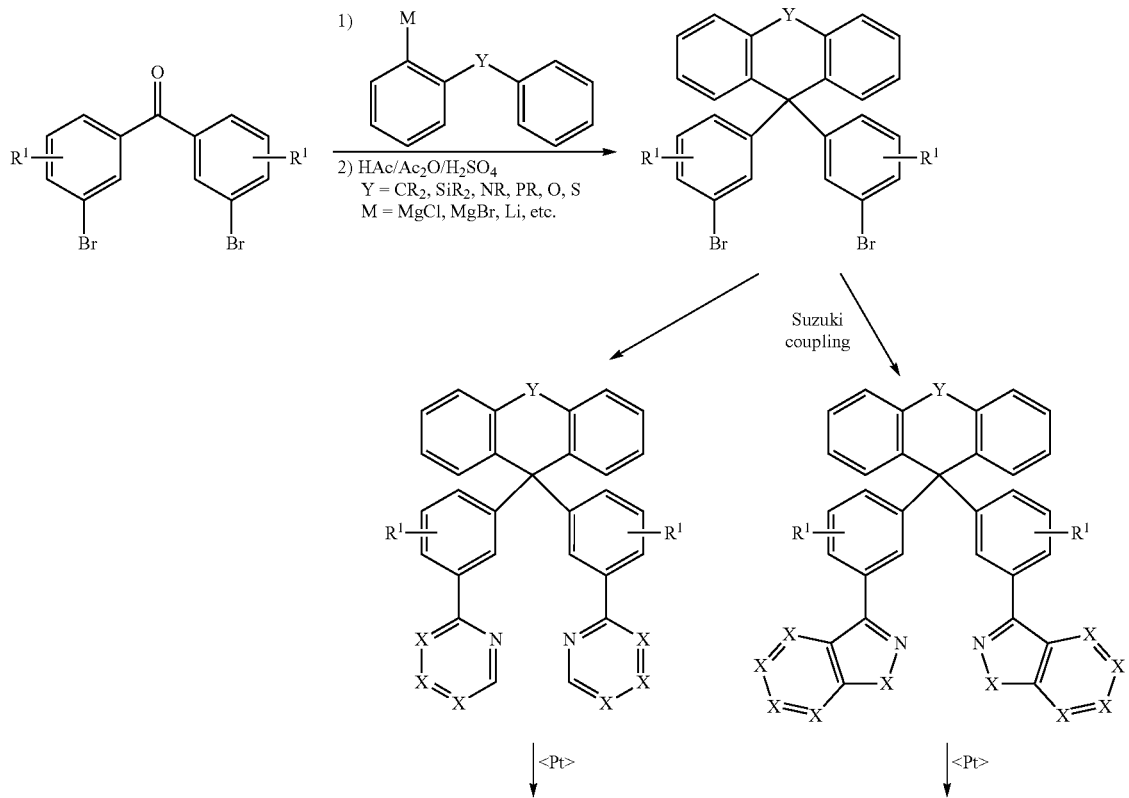

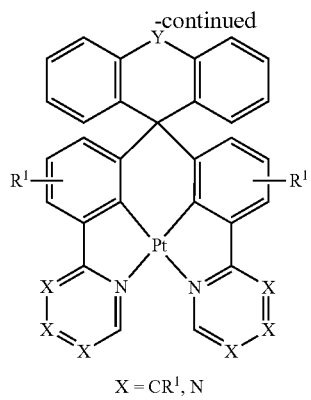

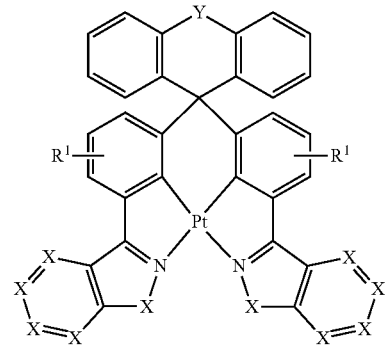

X = CR¹, N

The present invention therefore furthermore relates to a process for the preparation of the compounds of the formula (1) by reaction of the corresponding free ligands with a suitable metal compound. Suitable platinum starting materials are, for example, $PtCl_2$, $K_2[PtCl_4]$, $PtCl_2(DMSO)_2$, $Pt(Me)_2(DMSO)_2$, $PtCl_2(benzonitrile)_2$, $PtCl_2(acetonitrile)_2$ or Pt-olefin complexes, such as, for example, $(COD)PtCl_2$. Suitable iridium starting materials are, for example, iridium (III) chloride hydrate, iridium-olefin complexes, for example with COD as ligand, $Ir(acac)_3$, $Ir(tBu-acac)_3$ or Vaska's complex. Suitable gold starting materials are, for example, $AuCl_3$ or $HAuCl_4$.

The synthesis can also be activated thermally, photochemically and/or by microwave radiation. In a possible embodiment of the invention, the reaction is carried out in the melt without the use of an additional solvent. "Melt" here means that the ligand is in molten form and the metal precursor is dissolved or suspended in this melt. In a further possible embodiment of the invention, the corresponding free ligand is reacted with the metal precursor, for example $K_2PtCl_4$, in glacial acetic acid.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

Examples of suitable compounds according to the invention are the structures shown in the following table.

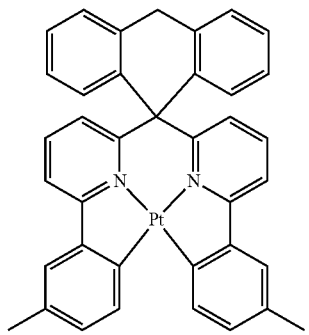
(1)

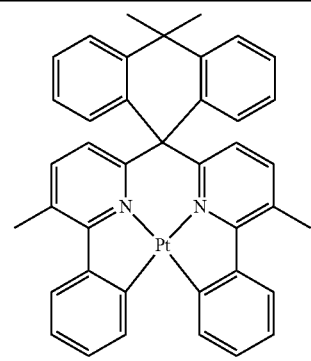
(2)

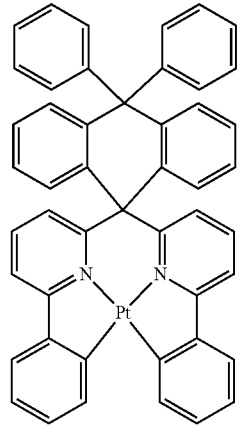
(3)

(4)
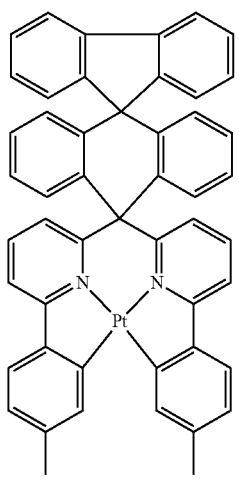
(5)
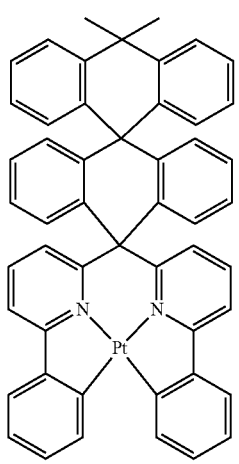
(6)
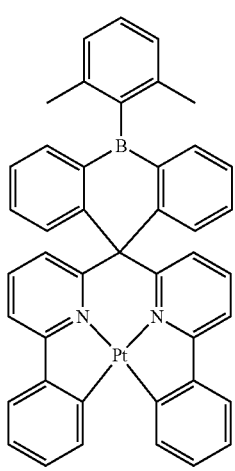
(7)
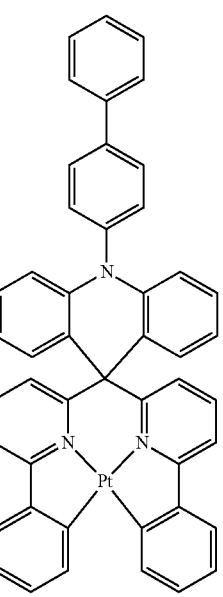
(8)
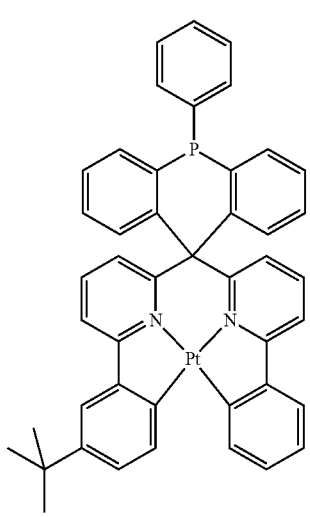
(9)
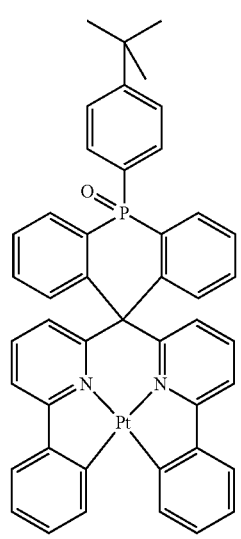

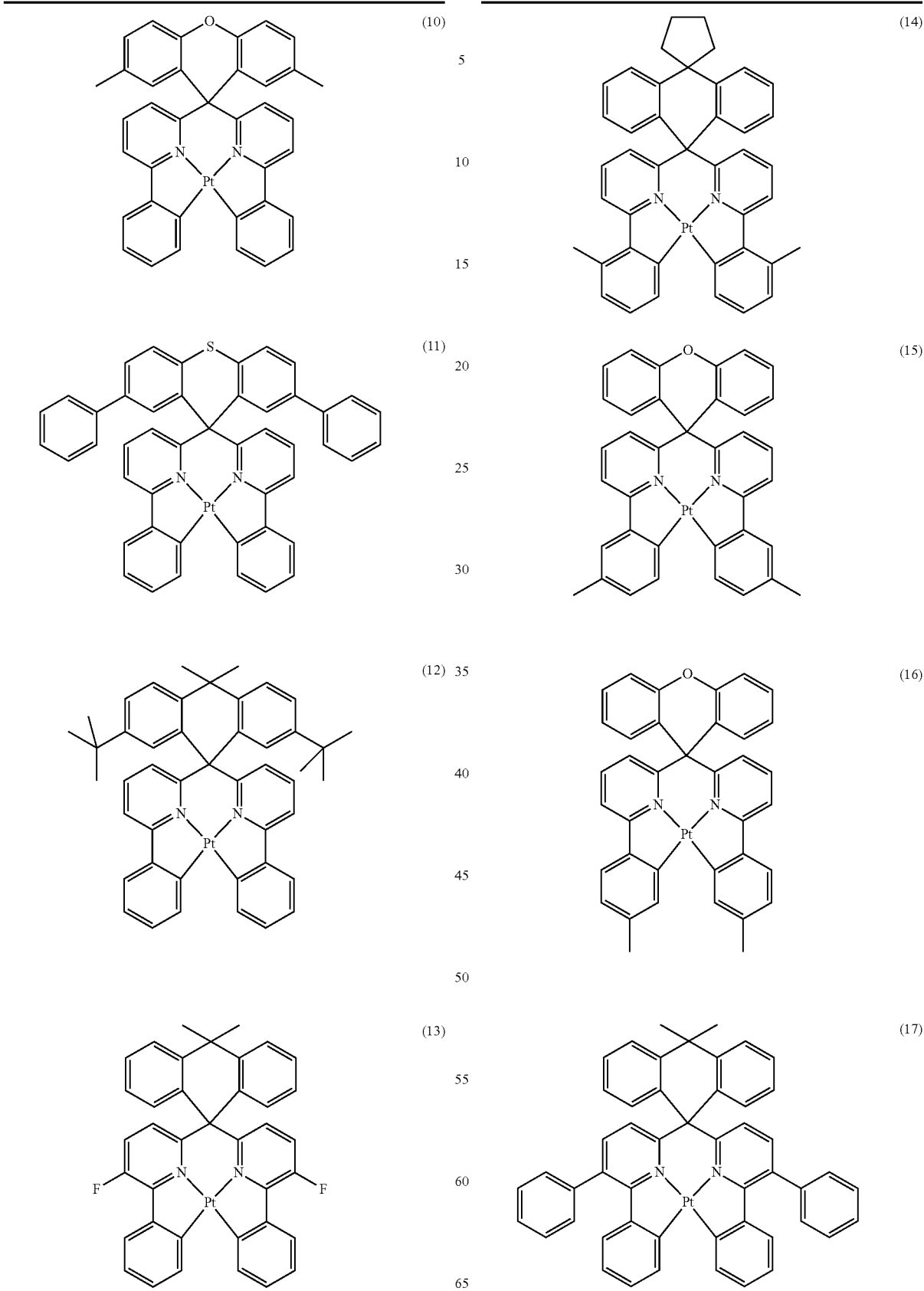

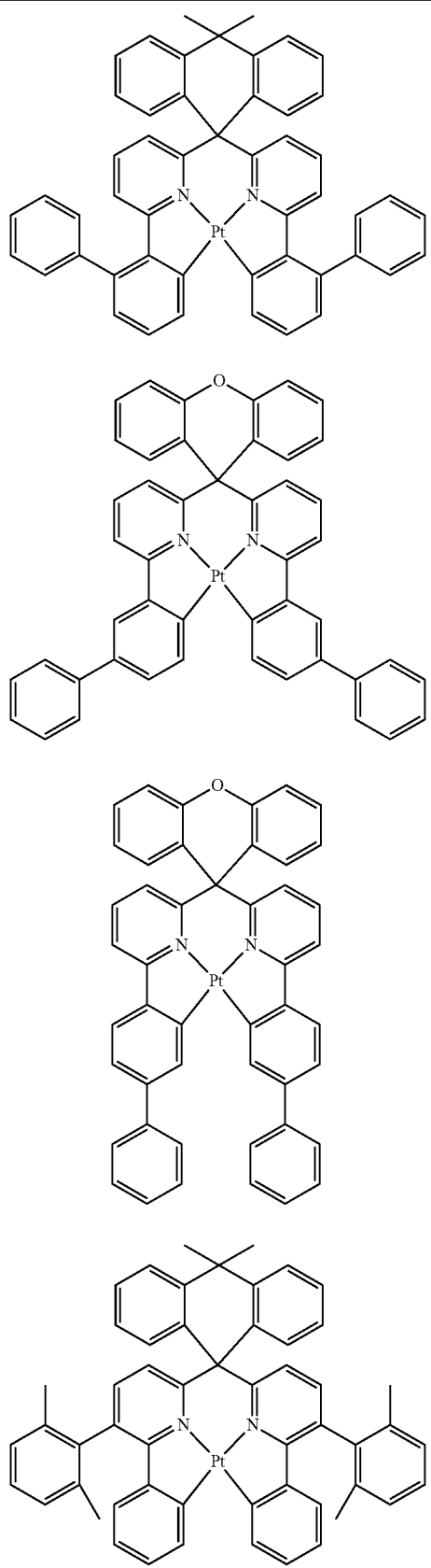
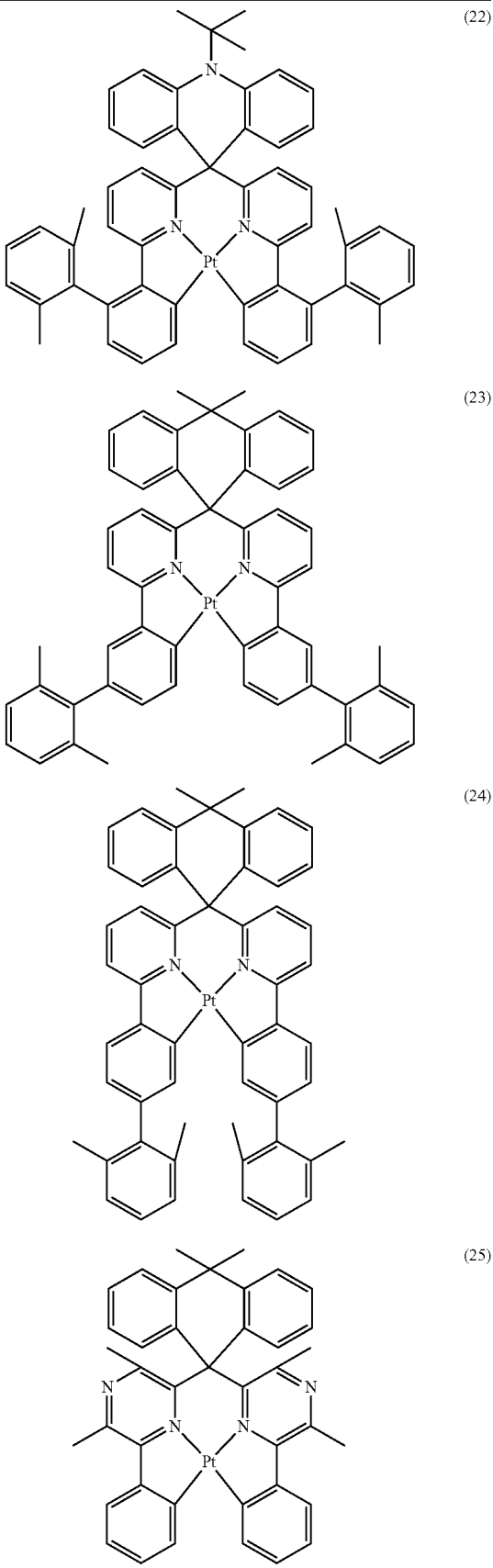

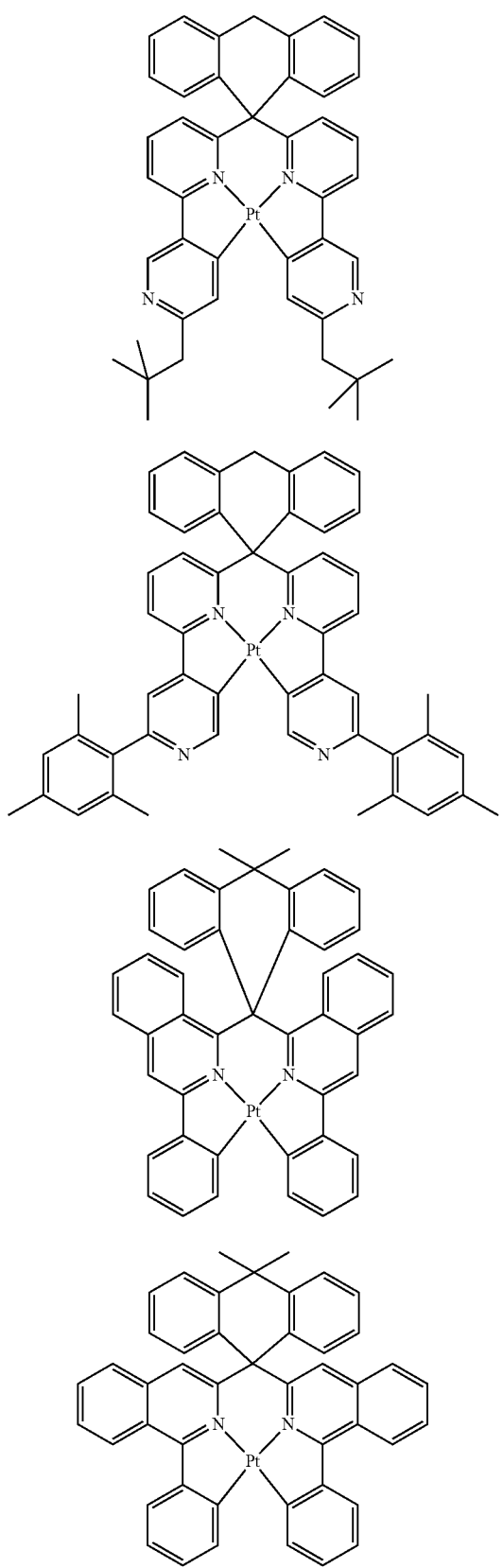
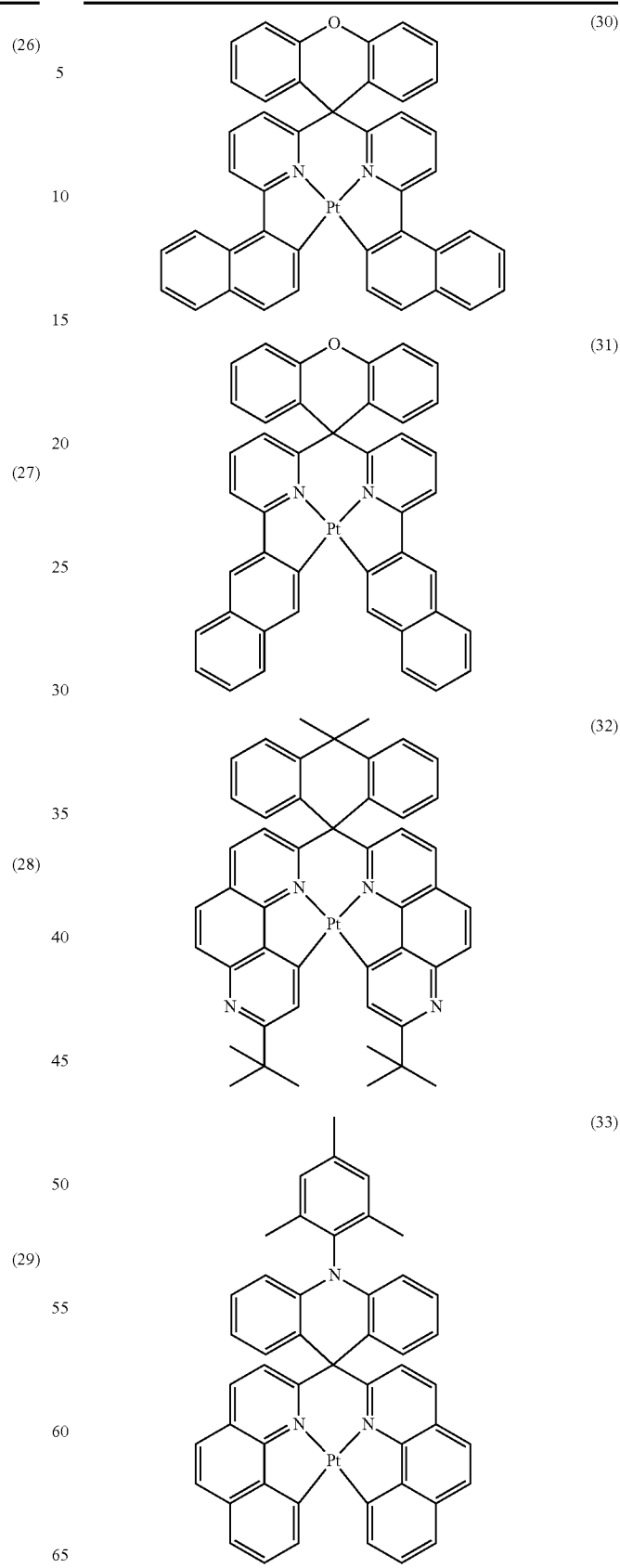

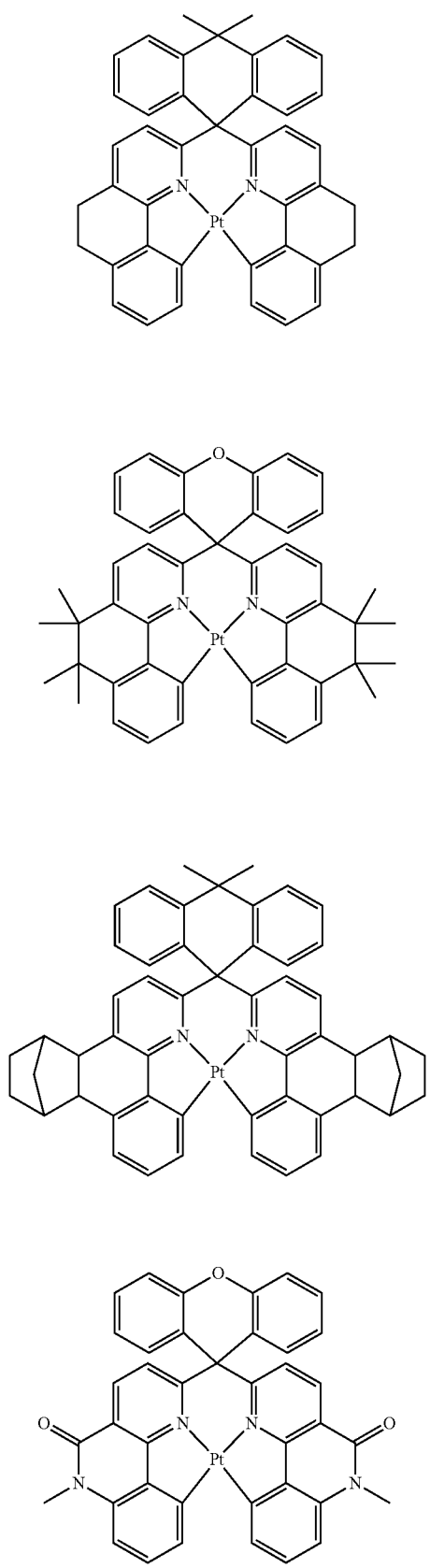
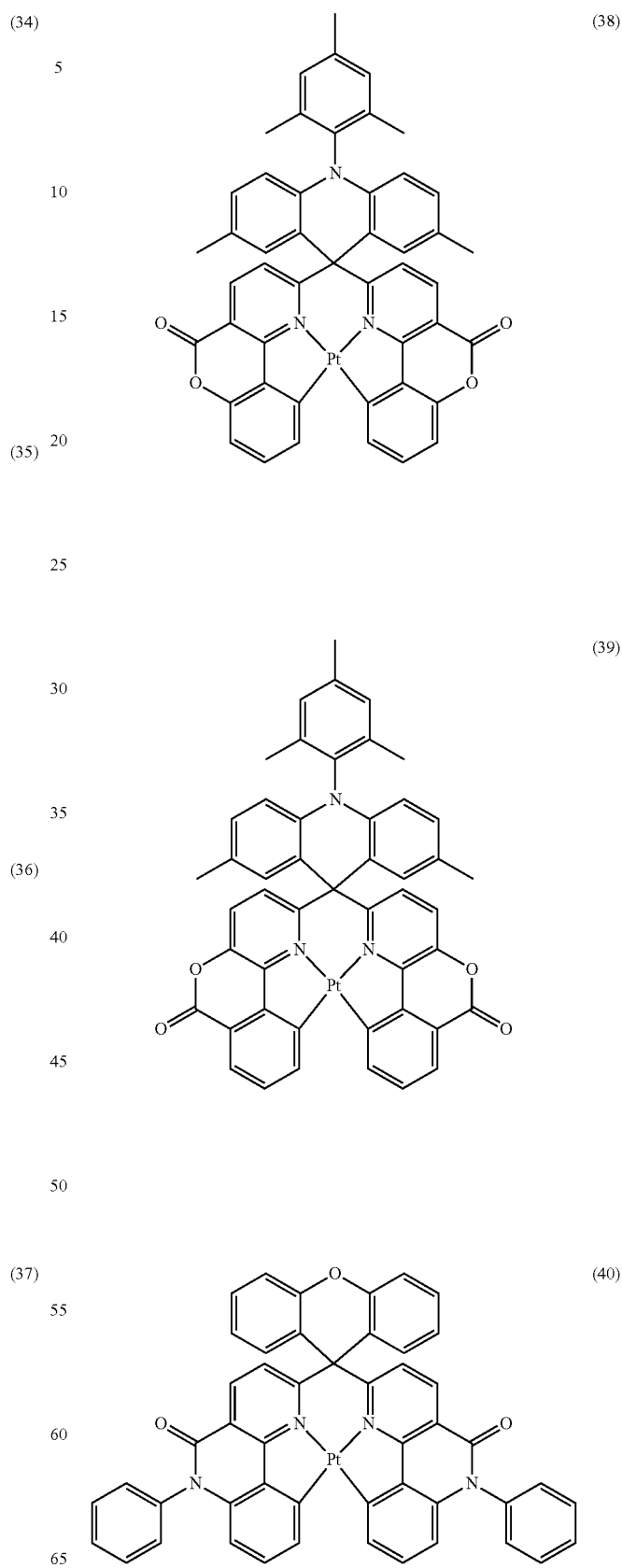

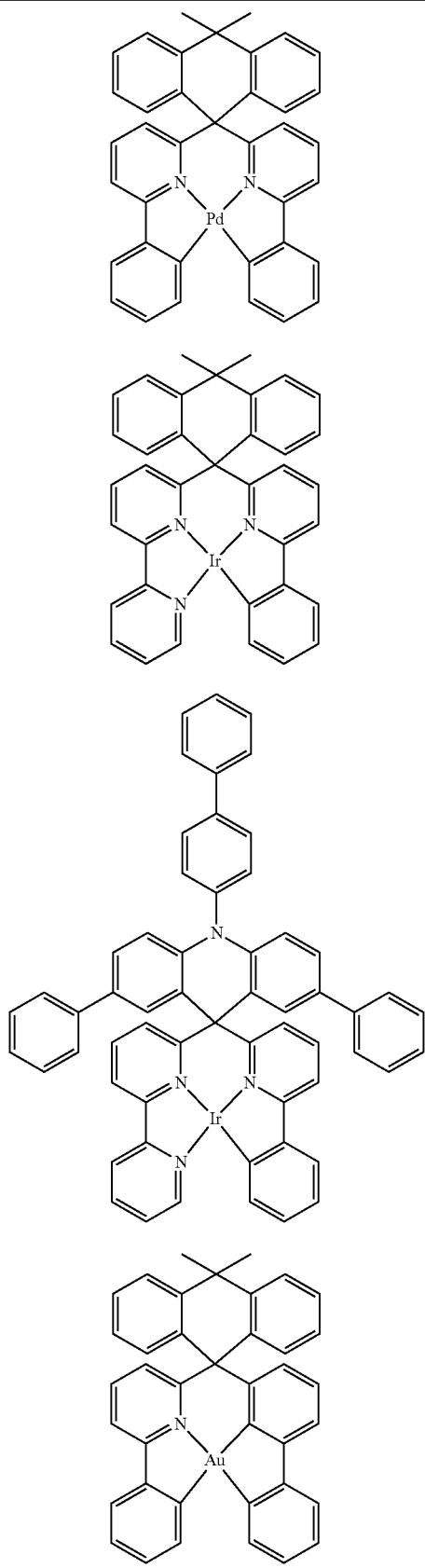
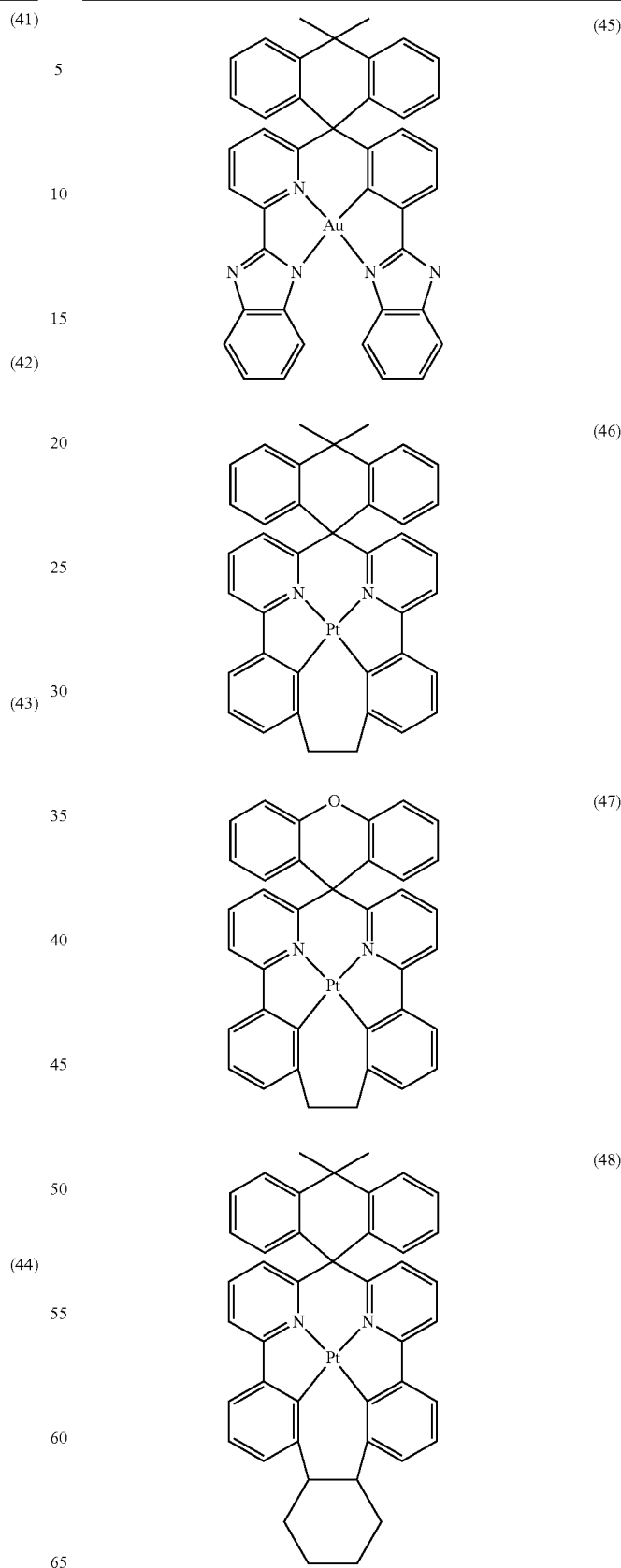

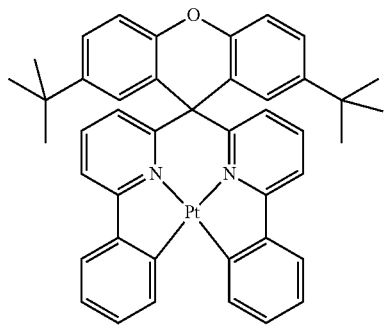 (49)
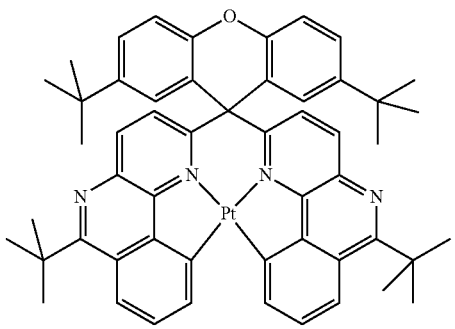 (53)
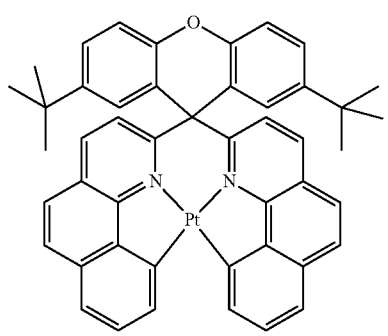 (50)
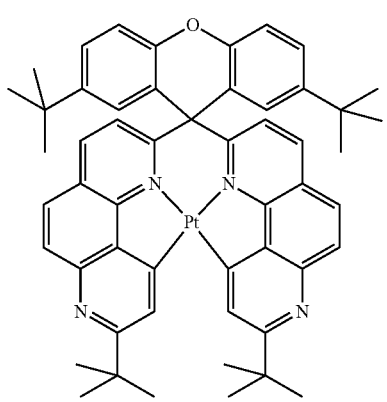 (54)
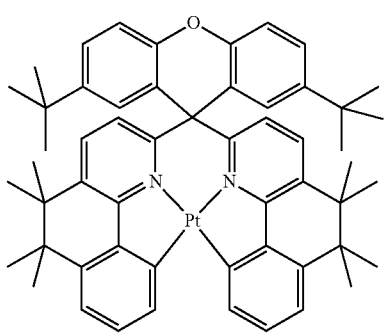 (51)
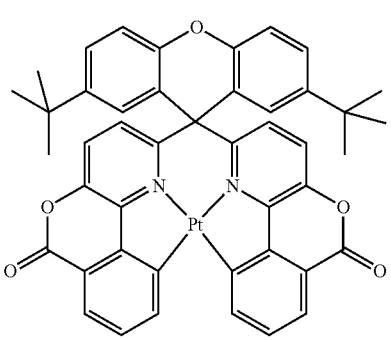 (55)
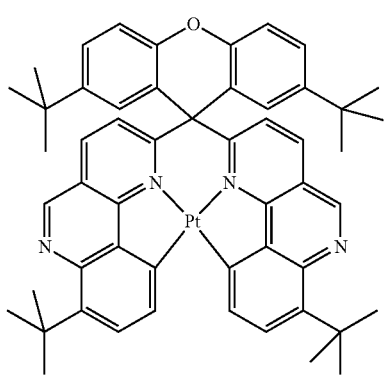 (52)
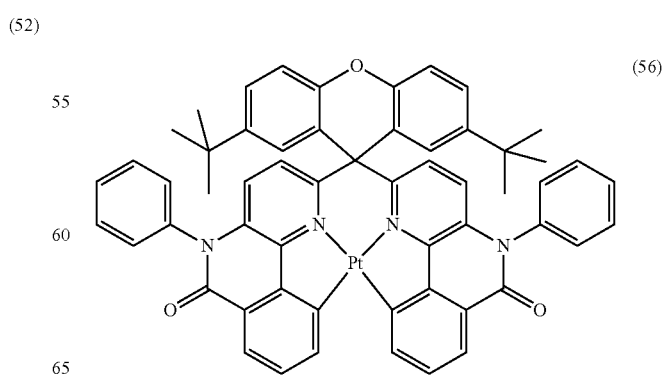 (56)

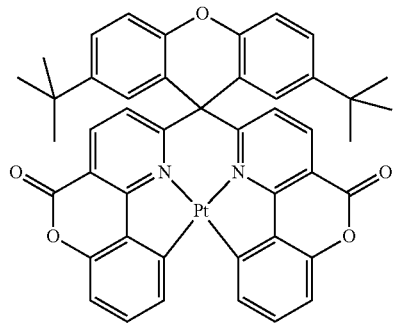
(57)
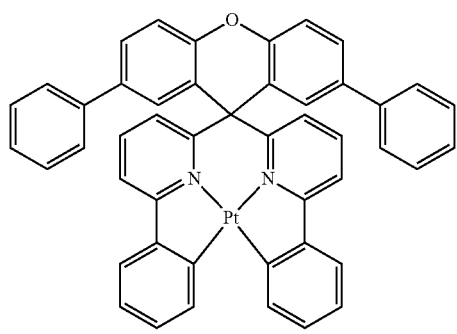
(58)
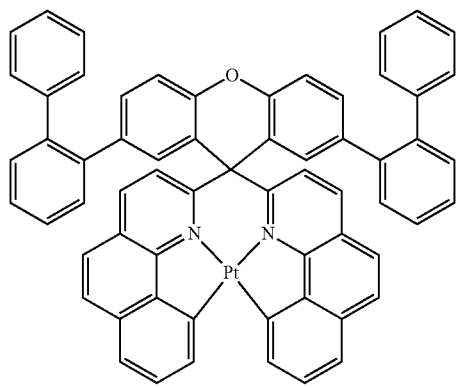
(59)
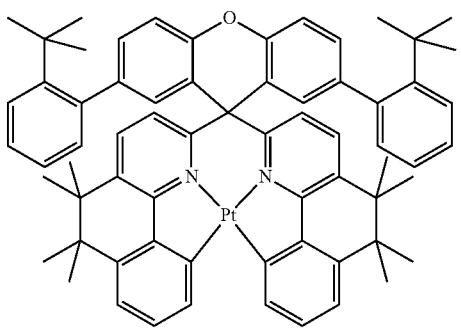
(60)
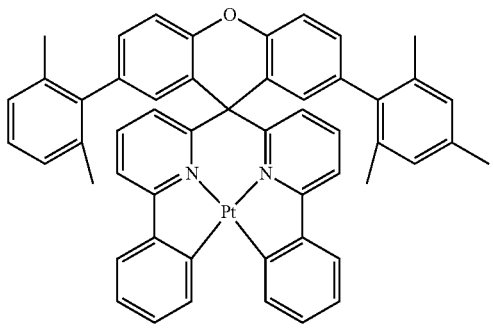
(61)
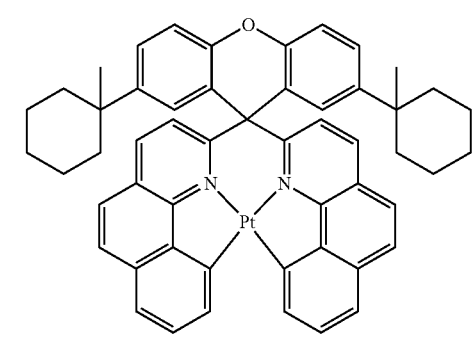
(62)
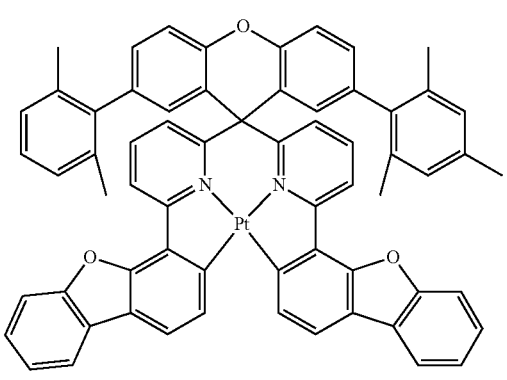
(63)
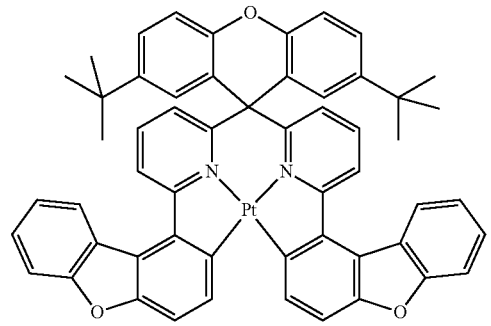
(64)

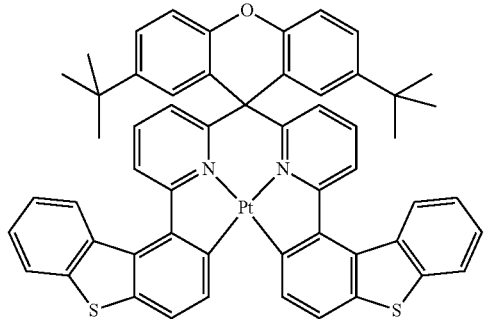
(65)
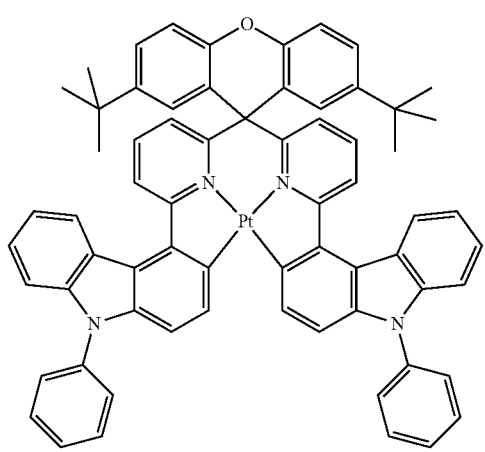
(66)
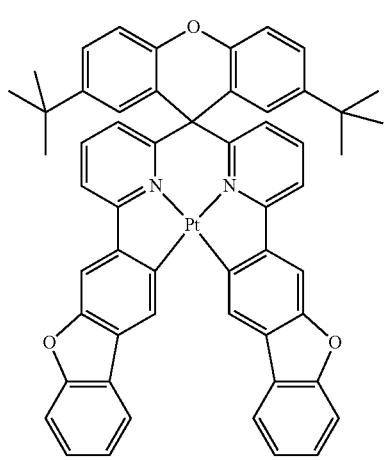
(67)
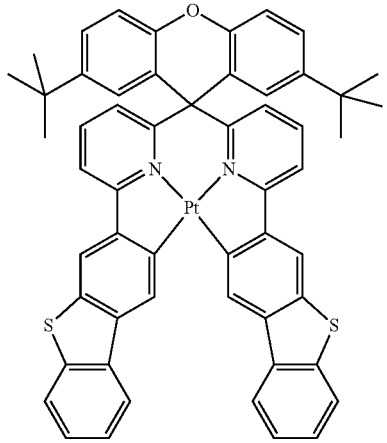
(68)
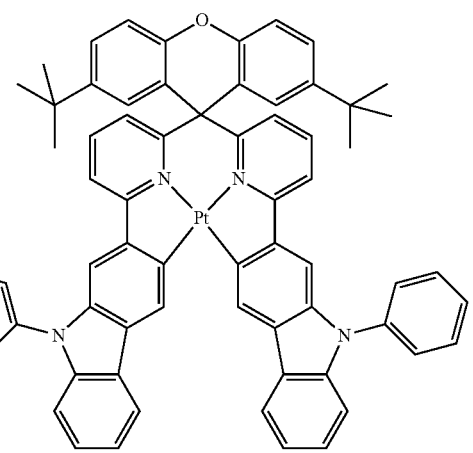
(69)
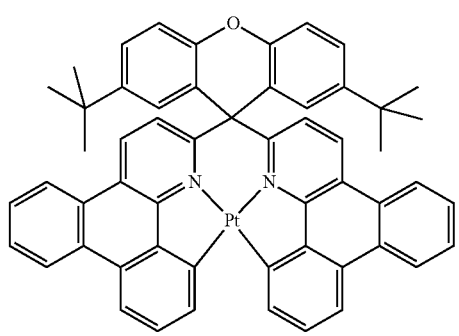
(70)
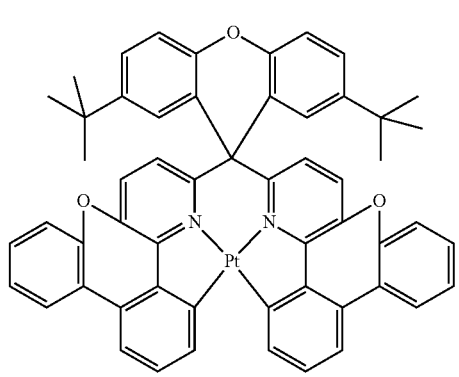
(71)

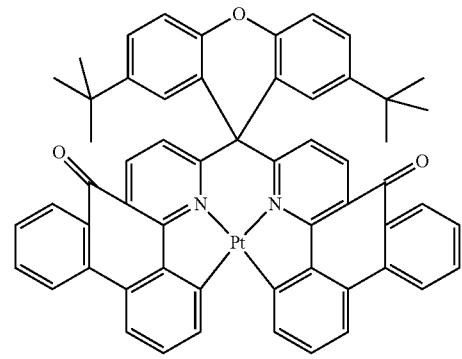
(72)
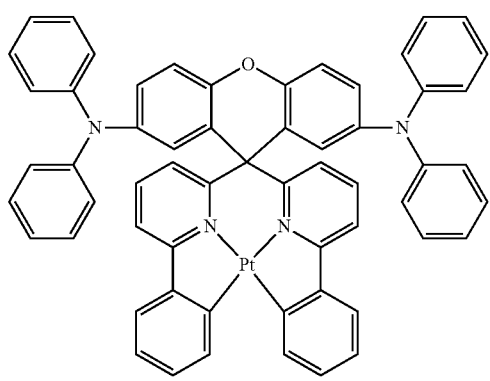
(73)
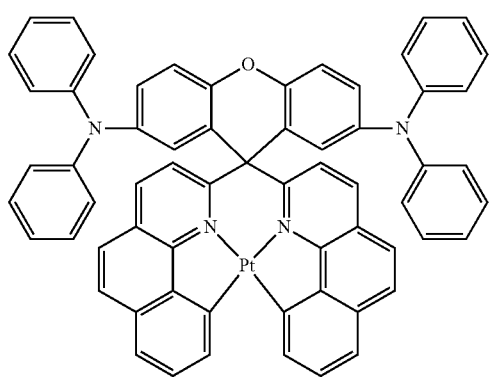
(74)
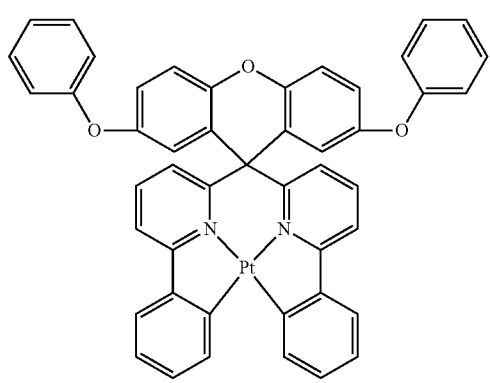
(75)
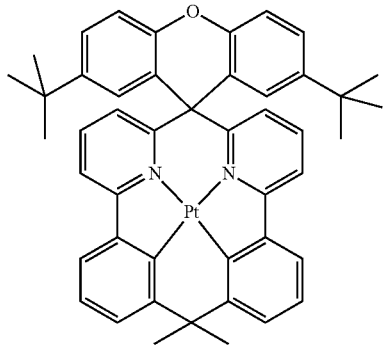
(76)
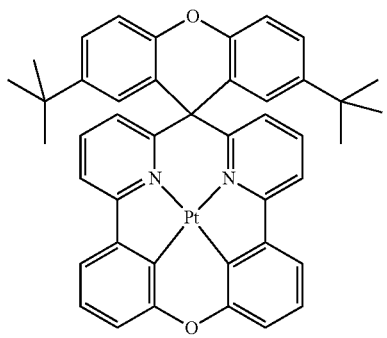
(77)
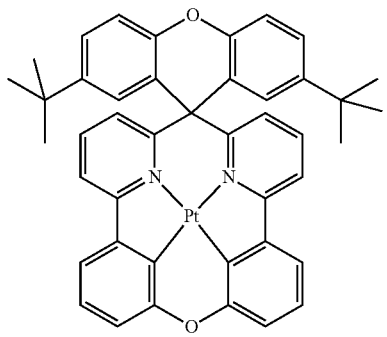
(78)
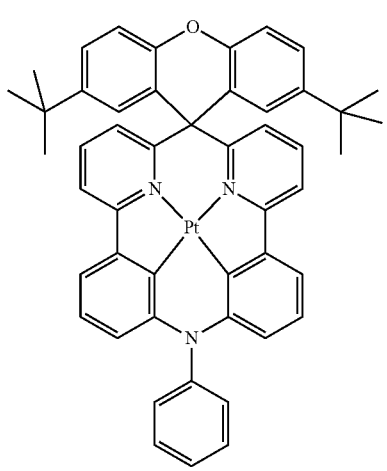
(79)

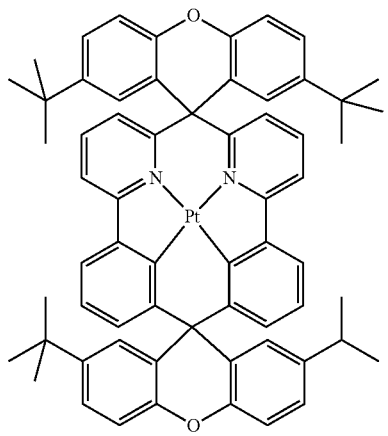
(80)
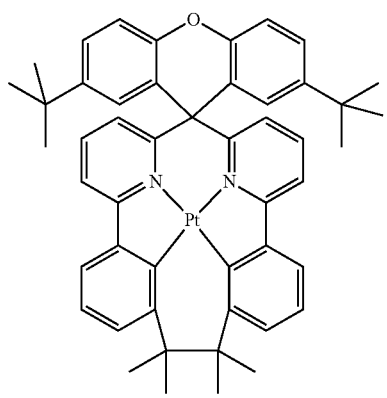
(81)
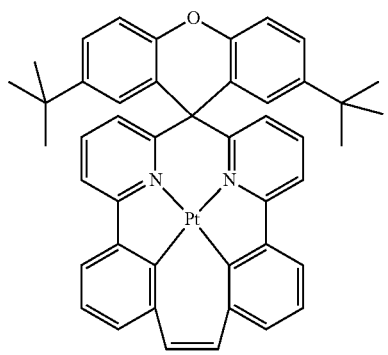
(82)
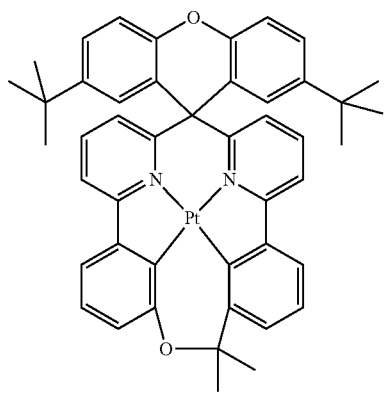
(83)
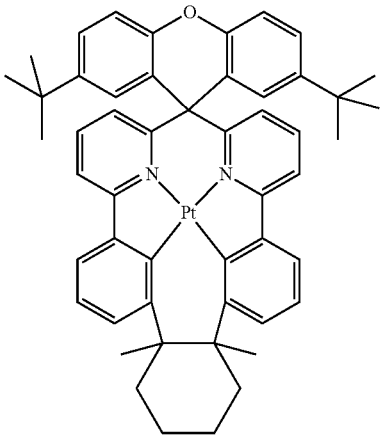
(84)
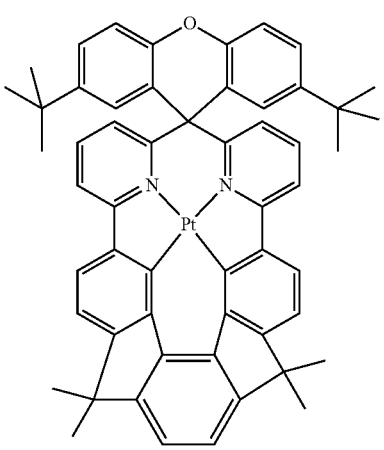
(85)
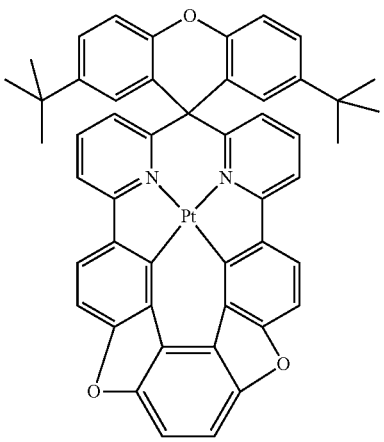
(86)

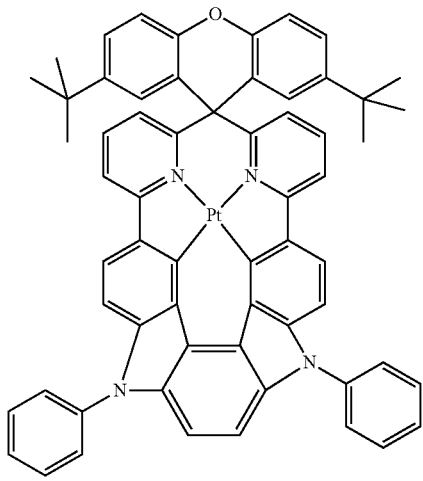
(87)
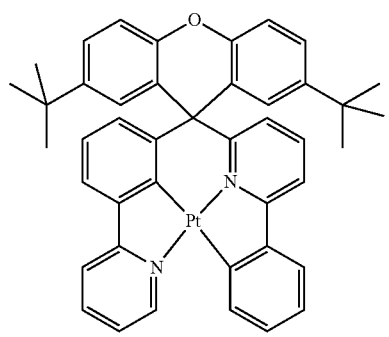
(88)
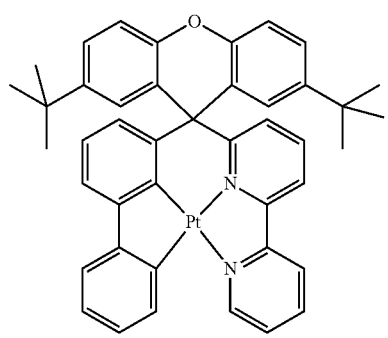
(89)
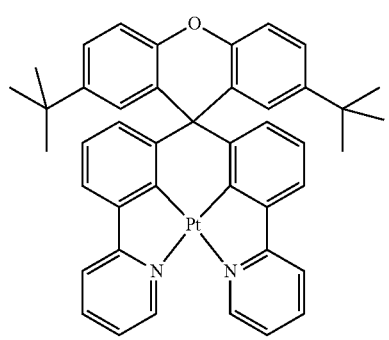
(90)
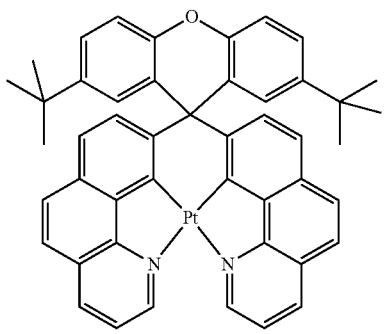
(91)
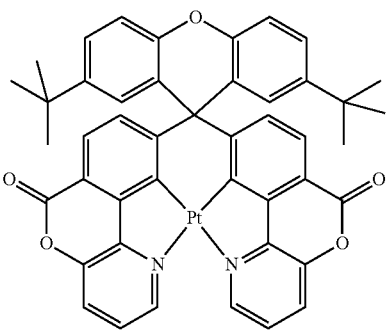
(92)
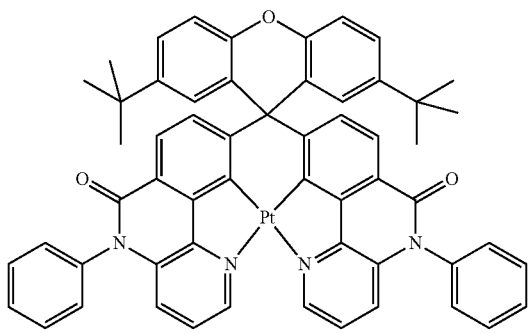
(93)
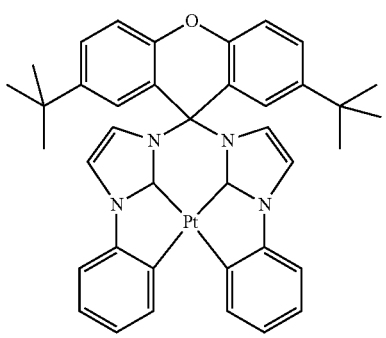
(94)

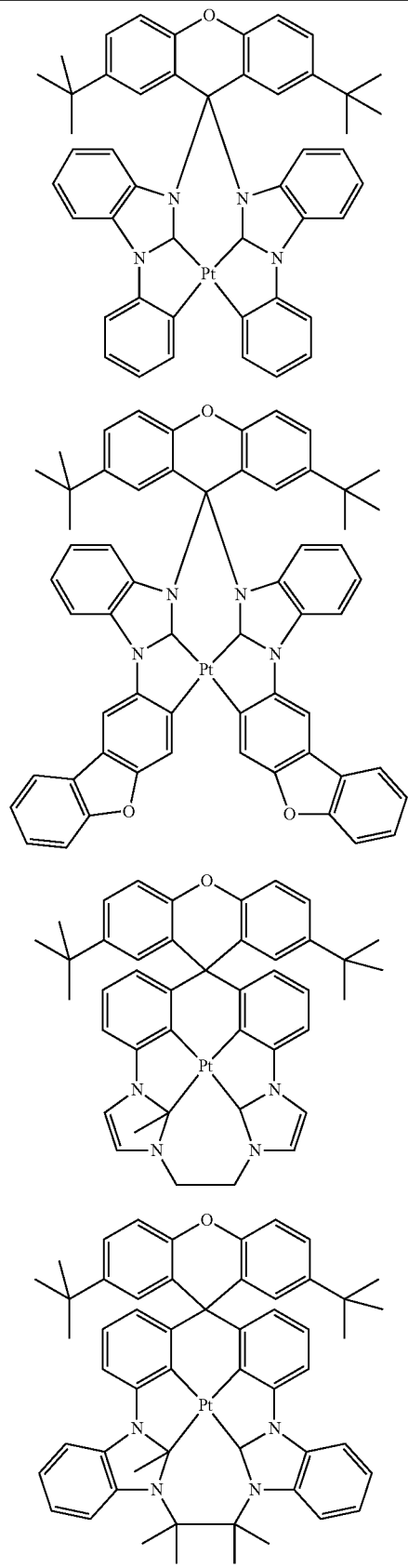
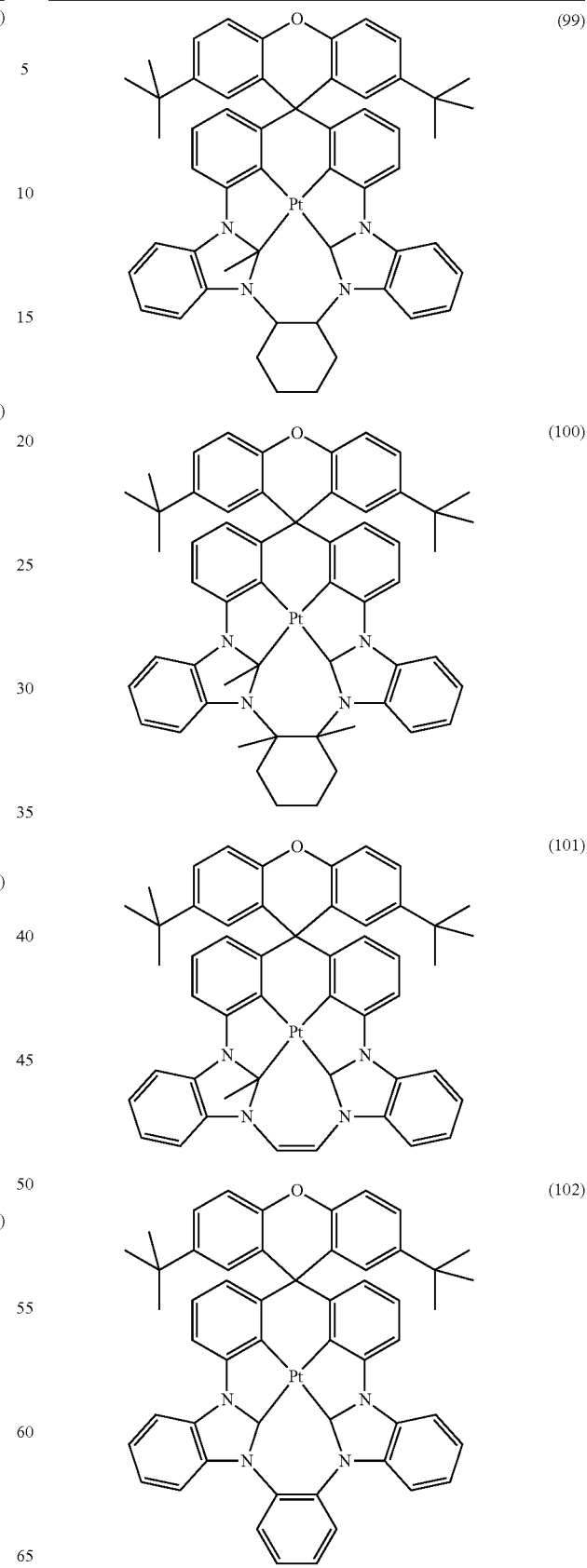

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. Compounds of this type are then soluble in common organic solvents, such as, for example, toluene or xylene, at room temperature in sufficient concentration to be able to process the complexes from solution. These soluble compounds are particularly suitable for processing, for example, by printing processes.

The present invention therefore furthermore relates to a formulation, in particular a solution, a suspension or a mini-emulsion, comprising at least one compound of the formula (1) or the preferred embodiments indicated above and at least one solvent.

The complexes of the formula (1) described above or the preferred embodiments indicated above can be used as active component in an electronic device. The present invention therefore furthermore relates to the use of a compound of the formula (1) or the preferred embodiments indicated above in an electronic device. The present invention furthermore relates to the use of a compound of the formula (1) or the preferred embodiments indicated above for the generation of singlet oxygen or in an oxygen sensor.

The present invention again furthermore relates to an electronic device comprising at least one compound of the formula (1) or the preferred embodiments indicated above. The electronic device according to the invention comprises anode, cathode and at least one layer which comprises at least one compound of the formula (1) given above. Preferred electronic devices here are selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) or oxygen sensors, comprising at least one compound of the formula (1) indicated above or the preferred embodiments indicated above in at least one layer. Particular preference is given to organic electroluminescent devices. The term active components is generally applied to the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one or more emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) or the preferred embodiments indicated above is employed as emitting compound in an emitting layer, it is preferably employed in combination with one or more matrix materials. A matrix material in the sense of the present invention is a material which can be used in an emission layer in order to dope in the emitting material in typically a concentration by volume of <25%, but which does not itself contribute significantly to light emission, in contrast to the doped-in emitter material. What materials in an emitter layer contribute significantly to light emission and what do not, and what materials should thus be regarded as emitters and what should be regarded as matrix materials can be recognised by a comparison of the electroluminescence spectrum of the OLED in which the emitter layer is present with photoluminescence spectra of the individual materials. The mixture of the compound of the formula (1) or the preferred embodiments indicated above and the matrix material comprises between 0.1 and 99% by vol., preferably between 1 and 90% by vol., particularly preferably between 3 and 40% by vol., in particular between 5 and 15% by vol., of the compound of the formula (1) or the preferred embodiments indicated above, based on the entire mixture of emitter and matrix material. Correspondingly, the mixture comprises between 99.9 and 1% by vol., preferably between 99 and 10% by vol. particularly preferably between 97 and 60% by vol., in particular between 95 and 85% by vol., of the matrix material, based on the entire mixture of emitter and matrix material.

The matrix material employed can generally be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or the unpublished applications DE 102010005697.9, DE 102010012738.8, DE 102010019306.2 and EP 11003232.3.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-trans-porting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or red-emitting triplet emitters. The complexes according to the invention can likewise be employed as triplet emitters together with a metal complex emitting at shorter wavelength. Preference is given here to the combination of two platinum complexes or the combination of one platinum complex with one iridium complex.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished over the prior art by the following surprising advantages:

1. Organic electroluminescent devices comprising compounds of the formula (1) as emitting materials have a very long lifetime.
2. Organic electroluminescent devices comprising compounds of the formula (1) as emitting materials\at the same time have very good efficiency.

In particular, the compounds according to the invention exhibit an improvement with respect to efficiency and/or lifetime compared with compounds which either contain a group $CR_2$ in which the two groups R do not form a ring with one another as bridgehead, or which contain a fluorene as bridgehead, where the two part-ligands are each bonded at the 9-position.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are, unless indicated otherwise, carried out in dried solvents under a protective-gas atmosphere. The starting materials can be purchased, for example, from Sigma-ALDRICH or ABCR. The numbers in square brackets in the case of the starting materials which are known from the literature refer to the CAS numbers.

A: Synthesis of Synthones

Example 1

(2-Bromophenyl)phenyl-(2,4,6-trimethylphenyl) amine, S1

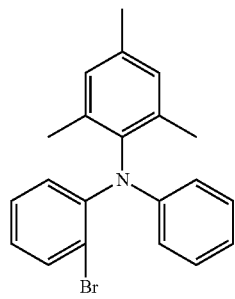 [SMILES: Cc1cc(C)c(N(c2ccccc2)c2ccccc2Br)c(C)c1]

1.0 g (5 mmol) of tri-tert-butylphosphine and 561 mg (2.5 mmol) of palladium(II) acetate are added to a mixture of 21.1 g (100 mmol) of phenyl-(2,4,6-trimethylphenyl)amine [23592-67-8], 31.1 g (110 mmol) of 1-bromo-2-iodobenzene [583-55-1] and 13.5 g (140 mmol) of sodium tert-butoxide in 600 ml of toluene, and the mixture is then heated under reflux for 20 h. After cooling to 60° C., 500 ml of water are added to the reaction mixture, the organic phase is separated off, washed twice with 300 ml of water each time and dried over magnesium sulfate. After removal of the toluene in vacuo, the residue is recrystallised from methanol with addition of a little ethyl acetate. Yield: 25.7 g (70 mmol), 70%; purity about 96% according to $^1$H-NMR.

Example 2

Bis(2-bromophenyl)bisphenylmethane, S2

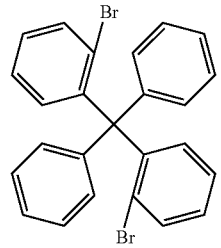 [SMILES: Brc1ccccc1C(c1ccccc1)(c1ccccc1)c1ccccc1Br]

100 ml (100 mmol) of a 1 M phenylmagnesium bromide solution are added dropwise to a solution of 34.0 g (100 mmol) of 2,2'-dibromobenzophenone [25187-01-3] in 500 ml of THF, and the mixture is subsequently stirred at 50° C. for 3 h. After addition of 300 ml of 1 N acetic acid and stirring for 30 min. at room temperature, the organic phase is separated off, diluted with 300 ml of ethyl acetate, washed once with 500 ml of water and once with 500 ml of saturated sodium chloride solution, dried over magnesium sulfate and then evaporated to dryness in vacuo. The foam obtained in this way is dissolved in 300 ml of dichloromethane, 8.0 ml (110 mmol) of thionyl chloride and 2 drops of DMF are added, and the mixture is heated under reflux for 30 min. When the evolution of gas is complete, the mixture is evaporated to dryness in vacuo, the residue is taken up in 27.4 ml (300 mmol) of aniline and heated at 200° C. for 5 min. with stirring. The reaction mixture is allowed to cool to 80° C., a mixture of 150 ml of 2 N HCl and 120 ml of methanol is added, and the mixture is stirred under reflux for a further 30 min. After cooling, the solid is filtered off with suction, washed once with a little methanol, the solid is suspended in a mixture of 200 ml of ethanol and 30 ml of conc. sulfuric acid, the reaction mixture is cooled to −10° C. in an ice/sodium chloride bath, 25 ml (220 mmol) of isoamyl nitrite are added dropwise, and the mixture is stirred for a further 30 min. 50 ml of 50% by weight aqueous hypophosphoric acid are then added, the mixture is slowly warmed and is stirred under reflux for a further 30 min. After cooling, the solid is filtered off with suction, washed three times with 50 ml of ethanol each time and then recrystallised twice from dioxane. Yield: 32.6 g (68 mmol), 68%; purity about 97% according to $^1$H-NMR.

Example 3

9,9-Bis(6-bromopyridin-2-yl)-9,10-dihydroanthracene, S3

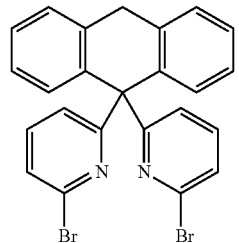 [SMILES: Brc1cccc(C2(c3cccc(Br)n3)c3ccccc3Cc3ccccc32)n1]

Variant A: Via Grignard Reagent

The corresponding Grignard reagent is prepared from 2.7 g (110 mmol) of iodine-activated magnesium turnings and a mixture of 24.7 g (110 mmol) of 2-bromophenylphenyl-methane [23450-18-2], 0.8 ml of 1,2-dichloroethane, 30 ml of 1,2-dimethoxyethane and 200 ml of THF with secondary heating using an oil bath at 70° C. When the magnesium has reacted completely, the mixture is allowed to cool to room temperature, and a solution of 34.2 g (100 mmol) of bis(6-bromopyridin-2-yl)methanone [42772-87-2] in 150 ml of THF is then added dropwise, and the mixture is then stirred at room temperature for a further 12 h. 100 ml of water are added, the mixture is then stirred briefly, the organic phase is separated off, and the solvent is removed in vacuo. The residue is suspended in 500 ml of warm glacial acetic acid at 40° C., 50 ml of acetic anhydride and then, dropwise, 10 ml of conc. sulfuric acid are added to the suspension. The solution obtained in this way is stirred at 80° C. for a further 1 h, the solvent is then removed in vacuo, the residue is taken up in 500 ml of dichloromethane, washed once with 500 ml of 2 N NaOH, once with 300 ml of water and once with 300 ml of saturated sodium chloride solution and then dried over magnesium sulfate. After removal of the dichloromethane in vacuo, the residue is recrystallised from 40 ml of ethyl acetate with addition of about 40 ml of ethanol. Yield: 27.6 g (56 mmol), 56%; purity about 98% according to $^1$H-NMR.

Variant B: Via Lithium Reagent 40.0 ml (100 mmol) of n-butyllithium (2.5 M in hexane) are added dropwise with stirring to a solution, cooled to −78° C., of 24.7 g (110 mmol) of 2-bromophenylphenyl-methane [23450-18-2] in 300 ml of THF. The mixture is stirred for a further 30 min., a solution of 34.2 g (100 mmol) of bis(6-bromopyridin-2-yl)methanone [42772-87-2] in 150 ml of THF is then added dropwise, and the mixture is allowed to warm slowly to room temperature. Further procedure as described in the case of Variant A. Yield: 23.2 g (47 mmol), 47%; purity about 96% according to $^1$H-NMR.

The following derivatives are prepared analogously:

| Ex. | Bromide Variant | Product | Yield |
|---|---|---|---|
| 4 | 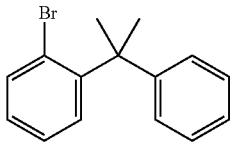[796966-97-7] A | 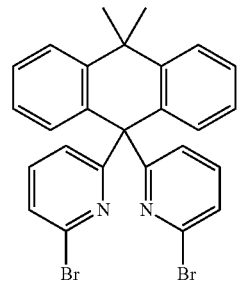S4 | 69% |
| 5 | 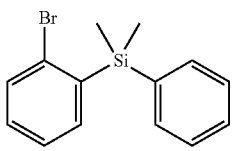[1160757-56-1] B | 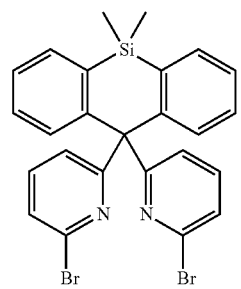S5 | 17% |
| 6 | 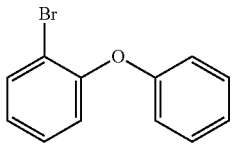[7025-06-1] A | 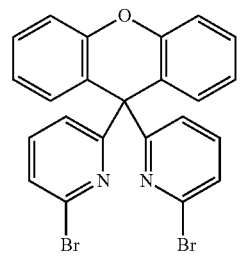S6 | 65% |

| Ex. | Bromide Variant | Product | Yield |
|---|---|---|---|
| 7 | 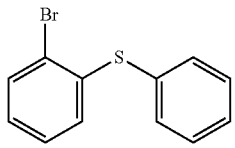<br>[15861-48-0]<br>B | 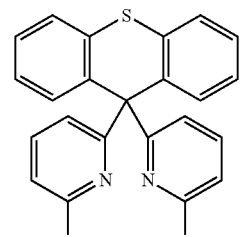<br>S7 | 69% |
| 8 | 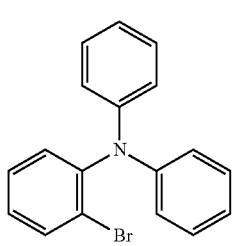<br>[78600-31-4]<br>B | 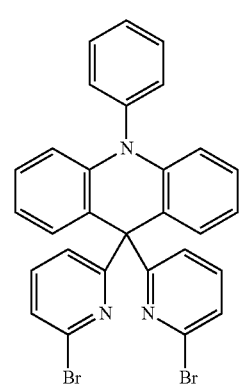<br>S8 | 58% |
| 9 | 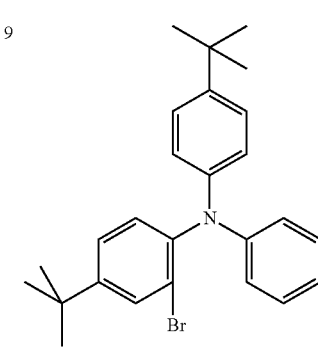<br>[911830-76-7]<br>B | 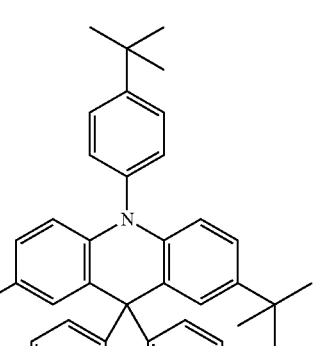<br>S9 | 54% |

-continued
| Ex. | Bromide Variant | Product | Yield |
|---|---|---|---|
| 10 | 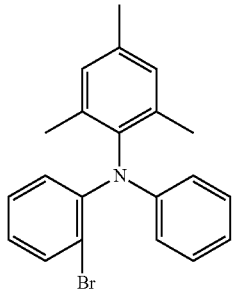<br>S1<br>B | 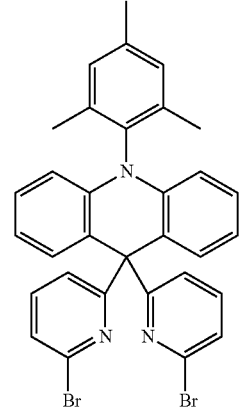<br>S10 | 60% |
| 11 | 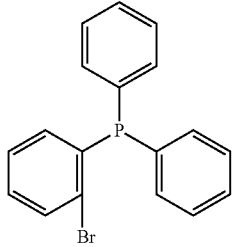<br>[62336-24-7]<br>B | 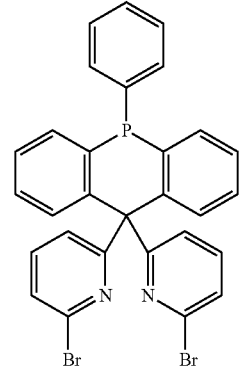<br>S11 | 44% |
| 12 | 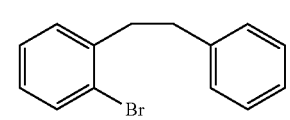<br>[57918-64-6]<br>A | 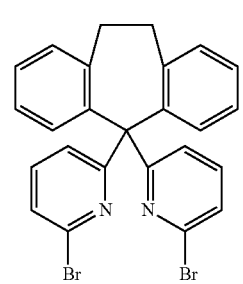<br>S12 | 30% |
| 13 | 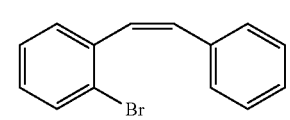<br>[4877-77-4]<br>B | 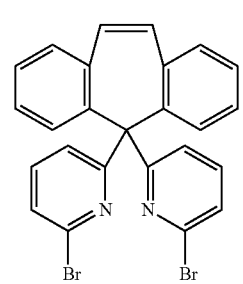<br>S13 | 18% |

| Ex. | Bromide Variant | Product | Yield |
|---|---|---|---|
| 14 | 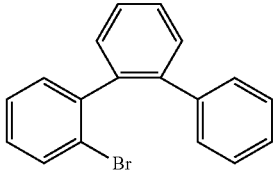 [75295-57-7] A | 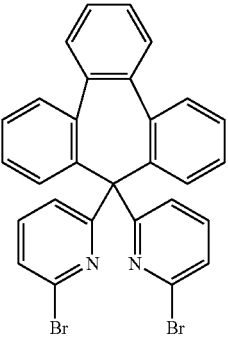 S14 | 42% |
| 15 | 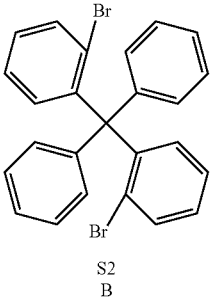 [SMILES: Brc1ccccc1C(c1ccccc1)(c1ccccc1)c1ccccc1Br] S2 B | 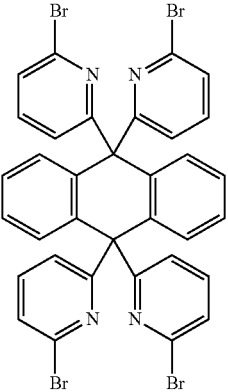 S15 | 23% |

Example 16

9,9-Bis(6-bromopyridin-2-yl)anthracen-9-one, S16

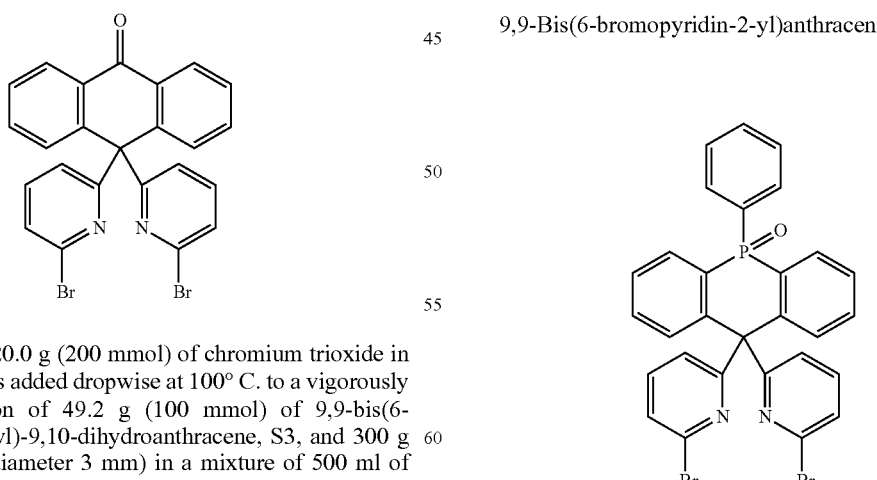

A solution of 20.0 g (200 mmol) of chromium trioxide in 200 ml of water is added dropwise at 100° C. to a vigorously stirred suspension of 49.2 g (100 mmol) of 9,9-bis(6-bromopyridin-2-yl)-9,10-dihydroanthracene, S3, and 300 g of glass beads (diameter 3 mm) in a mixture of 500 ml of acetic acid and 300 ml of water. The reaction mixture is stirred at 100° C. for a further 16 h, allowed to cool, 1000 ml of ethyl acetate are added, the mixture is washed three times with 500 ml of water each time, once with 500 ml of saturated sodium chloride solution, and the organic phase is dried over magnesium sulfate. The ethyl acetate is removed in vacuo, and the residue is recrystallised from toluene/cyclohexane. Yield: 35.4 g (70 mmol), 70%; purity about 96% according to $^1$H-NMR.

Example 17

9,9-Bis(6-bromopyridin-2-yl)anthracen-9-one, S17

27.1 g (110 mmol) of m-chloroperbenzoic acid, moist, 70%, are added in portions with stirring to a solution of 58.6 g (100 mmol) of 5,5-bis(6-bromopyridin-2-yl)-5,10-dihydro-10-phenylacridophosphine oxide, S11, in 500 ml of dichloromethane. After the mixture has been stirred for a further 16 h, the organic phase is washed once with 500 ml of 1 N NaOH and three times with 300 ml of water and dried over magnesium sulfate. After removal of the dichloromethane in vacuo, the residue is recrystallised from ethyl acetate with addition of ethanol. Yield: 47.1 g (78 mmol), 78%; purity about 97% according to $^1$H-NMR.

Example 18

9,9-Bis(6-bromopyridin-2-yl)-9,10-dihydroanthracene-10,10-spirobifluorene, S18

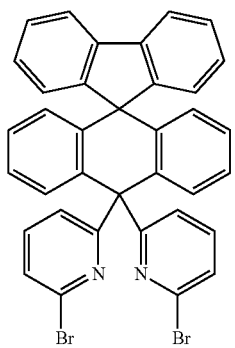 [SMILES: Brc1cccc(C2(c3cccc(Br)n3)c3ccccc3C3(c4ccccc4-c4ccccc43)c3ccccc32)n1]

The corresponding Grignard reagent is prepared from 2.7 g (110 mmol) of iodine-activated magnesium turnings and a mixture of 25.6 g (110 mmol) of 2-bromobiphenyl, 0.8 ml of 1,2-dichloroethane, 50 ml of 1,2-dimethoxyethane, 400 ml of THF and 200 ml of toluene with secondary heating using an oil bath at 70° C. When the magnesium has reacted completely, the mixture is allowed to cool to room temperature, and a solution of 50.6 g (100 mmol) of 9,9-bis(6-bromopyridin-2-yl)anthracen-9-one, S16, in 300 ml of THF is then added dropwise, and the mixture is stirred at room temperature for a further 12 h. 100 ml of water are added, the mixture is then stirred briefly, the organic phase is separated off, and the solvent is removed in vacuo. The residue is suspended in 500 ml of warm glacial acetic acid at 40° C., 0.2 ml of conc. sulfuric acid is added to the suspension, and the mixture is subsequently stirred at 100° C. for a further 2 h. The solvent is then removed in vacuo, the residue is taken up in 1000 ml of dichloromethane, washed once with 500 ml of 2 N NaOH, once with 300 ml of water and once with 300 ml of saturated sodium chloride solution and dried over magnesium sulfate. After removal of the dichloromethane in vacuo, the residue is recrystallised from dioxane. Yield: 48.8 g (76 mmol), 76%; purity about 98% according to $^1$H-NMR.

Synthesis of Ligands

Example 19

L1

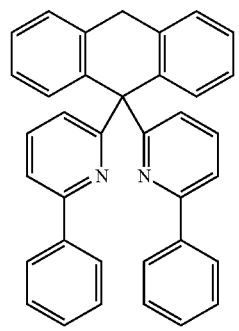 [SMILES: c1ccc(-c2cccc(C3(c4cccc(-c5ccccc5)n4)c4ccccc4Cc4ccccc43)n2)cc1]

526 mg (2.6 mmol) of tri-tert-butylphosphine and 449 mg (2 mmol) of palladium(II) acetate are added to a vigorously stirred mixture of 49.2 g (100 mmol) of 9,9-bis(6-bromopyridin-2-yl)-9,10-dihydroanthracene, S3, 48.8 g (400 mmol) of phenylboronic acid [98-80-6], 35.0 g (600 mmol) of potassium fluoride, anhydrous, and 700 ml of THF, and the mixture is then heated under reflux for 8 h. After cooling, the solvent is removed in vacuo, the residue is taken up in 500 ml of dichloromethane, washed three times with 300 ml of water each time and then dried over magnesium sulfate. After removal of the dichloromethane in vacuo, the residue is recrystallised from ethyl acetate/cyclohexane, and the solid is subsequently freed from readily volatile and nonvolatile components by fractional sublimation (p about 10$^{-5}$ mbar, T about 260-280° C.). Yield: 40.4 g (83 mmol), 83%; purity: about 99.0% according to $^1$H-NMR.

The following derivatives are prepared analogously:

| Ex. | Bromide/ boronic acid | Ligand | Yield |
|---|---|---|---|
| 20 | S4/ HO-B-OH (phenyl) [98-80-6] | L2 | 80% |

-continued
| Ex. | Bromide/boronic acid | Ligand | Yield |
|---|---|---|---|
| 21 | S4/ [123324-71-0] | L3 | 77% |
| 22 | S4/ [1174312-53-8] | L4 | 74% |
| 23 | S5 [98-80-6] | L5 | 23% |
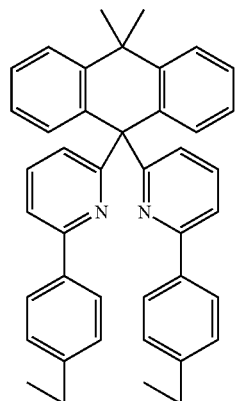 [SMILES: CC1(C)c2ccccc2C(c2cccc(-c3ccccc3)n2)(c2cccc(-c3ccccc3)n2)c2ccccc21]
-continued
| Ex. | Bromide/boronic acid | Ligand | Yield |
|---|---|---|---|
| 24 | S6 [98-80-6] | L6 | 80% |
| 25 | S6/ [1174312-53-8] | L7 | 77% |
| 26 | S6/ [150255-96-2] | L8 | 56% |
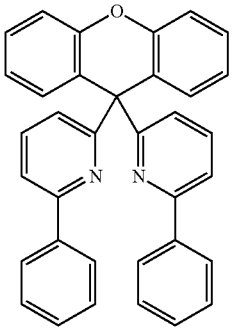
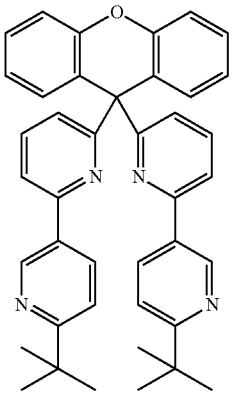
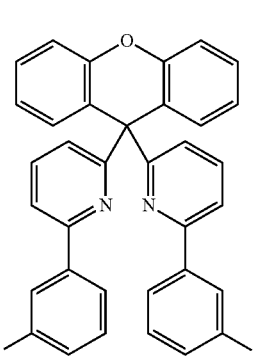
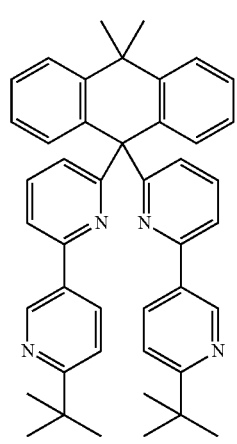
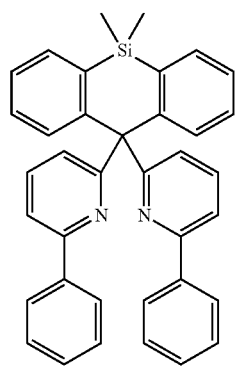

-continued

| Ex. | Bromide/boronic acid | Ligand | Yield |
|---|---|---|---|
| 27 | S6/ [144025-03-6] | L9 | 73% |
| 28 | S6/ [1034924-06-5] | L10 | 78% |
| 29 | S6/ [136466-94-9] | L11 | 68% |

-continued

| Ex. | Bromide/boronic acid | Ligand | Yield |
|---|---|---|---|
| 30 | S7/ [16419-60-6] | L12 | 75% |
| 31 | S7/ [590401-47-1] | L13 | 48% |
| 32 | S8/ [98-80-6] | L14 | 65% |

TABLE-continued

| Ex. | Bromide/boronic acid | Ligand | Yield |
|---|---|---|---|
| 33 | S8/ [16419-60-6] | L15 | 69% |
| 34 | S9/ [98-80-6] | L16 | 73% |
| 35 | S10/ [1174312-53-8] | L17 | 76% |
| 36 | S10/ [136466-94-9] | L18 | 63% |
| 37 | S11/ [98-80-6] | L19 | 34% |
| 38 | S12/ [1423-26-3] | L20 | 45% |

-continued

| Ex. | Bromide/ boronic acid | Ligand | Yield |
|---|---|---|---|
| 39 | S13/ [590401-47-1] | L21 | 26% |
| 40 | S14/ [113893-08-6] | L22 | 67% |
| 41 | S15/ [98-80-6] Use of 50 mmol of S15 | L23 | 63% |

-continued

| Ex. | Bromide/ boronic acid | Ligand | Yield |
|---|---|---|---|
| 42 | S16/ [98-80-6] | L24 | 75% |
| 43 | S16/ [1174312-53-8] | L25 | 76% |
| 44 | S17/ [98-80-6] | L26 | 69% |

| Ex. | Bromide/boronic acid | Ligand | Yield |
|---|---|---|---|
| 45 | S18/ 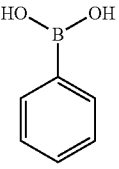 [98-80-6] | 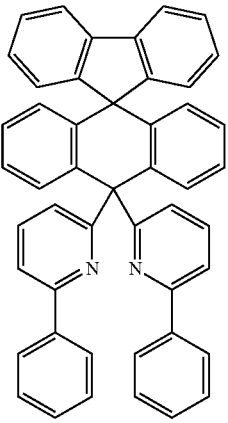 L27 | 74% |

Example 46

9,9-Bis(benzo[h]quinolin-2-yl)-10,10-dimethyl-9,10-dihydroanthracene, L28

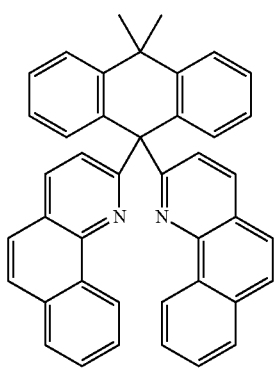 [SMILES: CC1(C)c2ccccc2C(c2ccc3ccc4ccccc4c3n2)(c2ccc3ccc4ccccc4c3n2)c2ccccc21]

a) Bisbenzo[h]quinolin-2-ylmethanone

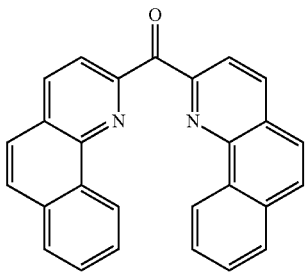 [SMILES: O=C(c1ccc2ccc3ccccc3c2n1)c1ccc2ccc3ccccc3c2n1]

80.0 ml (200 mmol) of n-butyllithium (2.5 M in n-hexane) are added dropwise to a solution, cooled to −78° C., of 51.6 g (200 mmol) of 2-bromo-benzo[h]quinoline [1097204-18-6] in 1000 ml of THF, and the mixture is stirred for a further 1 h. A mixture of 9.2 g (100 mmol) of N,N-dimethylcarbamoyl chloride [79-44-7] and 30 ml of THF is then added in one portion with vigorous stirring. The reaction mixture is allowed to warm slowly to room temperature, a mixture of 8 ml of acetic acid and 200 ml of water is added, the mixture is stirred at room temperature for a further 5 h, the aqueous phase is separated off, and the organic phase is evaporated to dryness. The residue is dissolved in about 300 ml of boiling DMF, 10 ml of water and 1 ml of acetic acid are added dropwise to the solution, and the mixture is stirred under reflux for a further 2 h. The mixture is allowed to cool to 80° C., 300 ml of EtOH are added dropwise, the mixture is allowed to cool to room temperature with stirring, the deposited crystals are filtered off with suction, washed twice with about 50 ml of EtOH and dried in vacuo. Yield: 26.2 g (68 mmol), 68%; purity about 97% according to $^1$H-NMR.

b) L28

Procedure analogous to Example 3, S3, using 30.3 g (110 mmol) of 1-bromo-2-(1-methyl-1-phenylethyl)benzene [796966-97-7] instead of 2-bromophenylphenylmethane and using 38.4 g (100 mmol) of bisbenzo[h]-quinolin-2-yl-methanone instead of bis(6-bromopyridin-2-yl)methanone. The solid is subsequently freed from readily volatile and non-volatile components by fractional sublimation (p about $10^{-5}$ mbar, T about 260-280° C.). Yield: 23.1 g (41 mmol), 41%; purity: about 99.0% according to $^1$H-NMR.

The following derivatives are prepared analogously:

| Ex. | Bromide/Variant | Product | Yield |
|---|---|---|---|
| 47 | 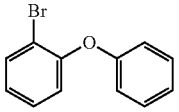 [7025-06-1] A | 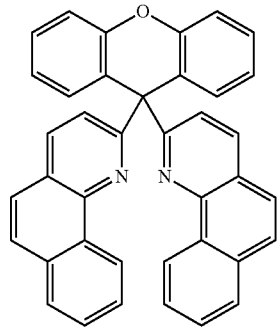 L29 | 46% |
| 48 | 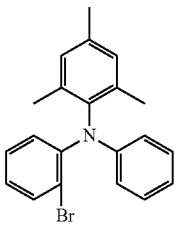 B | 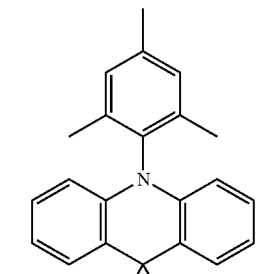 L30 | 43% |

Example 59

L31

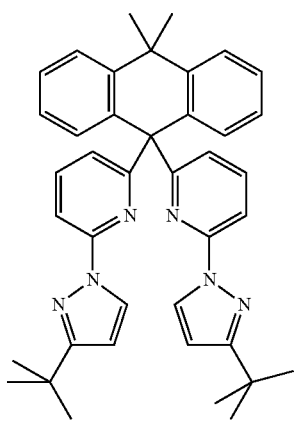 [SMILES: CC(C)(C)c1ccn(-c2cccc(C3(c4cccc(-n5ccc(C(C)(C)C)n5)n4)c4ccccc4C(C)(C)c4ccccc43)n2)n1]

A mixture of 52.0 g (100 mmol) of S4, 31.0 g (250 mmol) of 3-tert-butyl-1H-pyrazole [15802-80-9], 3.8 g (20 mmol) of copper(I) iodide, 200 g of glass beads (diameter 3 mm) and 200 ml of nitrobenzene is heated at 200° C. for 2 h. After cooling, the mixture is diluted with 1000 ml of dichloromethane, the glass beads and the salts are filtered off, and the mixture is evaporated to dryness in vacuo. The residue is taken up in 500 ml of THF, filtered through silica gel in order to remove dark components, then evaporated to about 100 ml, methanol (about 200 ml) is added to the warm mixture until crystallisation commences, the mixture is allowed to cool with stirring, the solid is filtered off with suction, washed three times with about 50 ml of methanol each time and dried in vacuo. The solid is subsequently freed from readily volatile and non-volatile components by fractional sublimation (p about $10^{-5}$ mbar, T about 260-280° C.). Yield: 27.3 g (45 mmol), 45%; purity: about 99.0% according to $^1$H-NMR.

The following derivative is prepared analogously:

| Ex. | Pyrazole | Product | Yield |
|---|---|---|---|
| 50 | H, F₃C, 7025-06-1 | L32 (F₃C, CF₃) | 38% |

Synthesis of Metal Complexes

Example 51

Synthesis of Platinum Complexes

Variant A:

A vigorously stirred mixture of 10 mmol of potassium tetrachloroplatinate, 10 mmol of the ligand L, 150 g of glass beads (diameter 3 mm) and 300 ml of glacial acetic acid is heated under reflux for 48 to 60 h until the o-metallation is complete. After dropwise addition of a mixture of 300 ml of water and 300 ml of ethanol to the cooled reaction mixture, the solid is filtered off with suction, washed five times with 25 ml of ethanol each time and dried in vacuo. The solid is suspended in 100 ml of glacial acetic acid, 20 ml of pyridine and 2.0 g of zinc dust are added to the suspension, and the mixture is stirred at 60° C. for 12 h. After cooling, the solid is filtered off with suction, washed three times with 25 ml of ethanol each time and dried in vacuo. The solid obtained in this way is placed on a Celite bed with a depth of 3 cm in a hot extractor and extracted with toluene (initially introduced amount about 200 ml). Metal complexes which have excessively good solubility in the extractant are brought to crystallisation by dropwise addition of 200 ml of ethanol. The solid of the suspensions obtained in this way is filtered off with suction, washed once with about 50 ml of ethanol and dried. After drying, the purity of the metal complex is determined by means of NMR and/or HPLC. If the purity is below 99.5%, the hot-extraction step is repeated; when a purity of 99.5-99.9% has been reached, the Pt complex is sublimed. The sublimation is carried out in a high vacuum (p about $10^{-6}$ mbar) in the temperature range from about 320 to about 380° C., where the sublimation is preferably carried out in the form of a fractional sublimation.

Variant B:

A mixture of 10 mmol of bis(benzonitrile)platinum(II) dichloride and 10 mmol of the ligand L in 100 ml of benzonitrile is heated under reflux for 6 to 48 h until the o-metallation is complete. After dropwise addition of 100 ml of ethanol to the cooled reaction mixture, the solid is filtered off with suction, washed five times with 25 ml of ethanol each time and dried in vacuo. Further procedure as described under variant A.

The following derivatives are prepared analogously:

| Ex. | Ligand | Pt complex/Variant | Yield |
|---|---|---|---|
| 52 | | | 41% |
| | | A | |
| 53 | L2 | PtL2 A | 38% |
| 54 | L3 | PtL3 A | 37% |

| Ex. | Ligand | Pt complex/Variant | Yield |
|---|---|---|---|
| 55 | L4 | PtL4 B | 44% |
| 56 | L5 | PtL5 B | 13% |
| 57 | L6 | PtL6 A | 45% |
| 58 | L7 | PtL7 B | 47% |
| 59 | L8 | PtL8 B | 46% |
| 60 | L9 | PtL9 B | 43% |
| 61 | L10 | PtL10 B | 38% |
| 62 | L11 | PtL11 B | 28% |
| 63 | L12 | PtL12 A | 35% |
| 64 | L13 | PtL13 A | 38% |
| 65 | L14 | PtL14 A | 41% |
| 66 | L15 | PtL15 A | 44% |
| 67 | L16 | PtL16 B | 40% |
| 68 | L17 | PtL17 B | 36% |
| 69 | L18 | PtL18 B | 43% |
| 70 | L19 | PtL19 A | 38% |
| 71 | L20 | PtL20 B | 35% |
| 72 | L21 | PtL21 B | 16% |
| 73 | L22 | PtL22 B | 37% |
| 74 | L23 Use of 20 mmol of K₂PtCl₄ | PtL23 A | 23% |
| 75 | L24 | PtL24 A | 45% |
| 76 | L25 | PtL25 B | 46% |
| 77 | L26 | PtL26 A | 39% |
| 78 | L27 | PtL27 B | 46% |
| 79 | L28 | PtL28 B | 40% |
| 80 | L29 | PtL29 B | 46% |
| 81 | L30 | PtL30 B | 41% |
| 82 | L31 | PtL31 B | 36% |
| 83 | L32 | PtL32 B | 28% |

Example 84

Production of OLEDs

OLEDs according to the invention and OLEDs in accordance with the prior art are produced by a general process in accordance with WO 2004/058911, which is adapted to the circumstances described here (layer-thickness variation, materials used).

The results of various OLEDs are presented in the following examples (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have basically the following layer structure:

Substrate
Hole-injection layer 1: HIL1, 10 nm
Hole-injection layer 2: HIL2, 10 nm
Hole-injection layer 3: HIL1, 200 nm
Hole-injection layer 4: HIL2, 10 nm
Hole-transport layer 1: HTL1, 20 nm
Electron-blocking layer 1: EBL1, optional, see Table 1, 10 nm Emission layer: see Table 1
Hole-blocking layer 1: M1, 10 nm
Electron-transport layer: ETM1+LiQ, 50%:50%, 30 nm
Cathode: aluminium, 100 nm For the vacuum-processed OLEDs, all materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as M1:M2:PtL (55%:35%:10%) here means that material M1 is present in the layer in a proportion by volume of 55%, M2 is present in the layer in a proportion of 35% and the emitter PtL is present in the layer in a proportion of 10%. Analogously, the electron-transport layer likewise consists of a mixture of two materials. The precise structure of the emission layer is shown in Table 1. The materials used for the production of the OLEDs are shown in Table 3.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT50 means that the lifetime given is the time at which the luminous density has dropped to 50% of the initial luminous density, i.e. from, for example, 4000 cd/m$^2$ to 2000 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

Use of Compounds According to the Invention as Emitter Materials in Phosphorescent OLEDs The compounds according to the invention can be employed, inter alia, as phosphorescent emitter materials in the emission layer in OLEDs. In the case of the OLEDs, it is evident here that the materials according to the invention result in efficient blue-, green- or red-emitting OLEDs.

TABLE 1

Use of compounds according to the invention as emitters in phosphorescent OLEDs

| Ex. | EBL | EML/thickness |
|---|---|---|
| 85 | — | M1:M2:PtL1 (80%:15%:5%) 30 nm |
| 86 | — | M1:M2:PtL2 (80%:15%:5%) 30 nm |
| 87 | — | M1:M2:PtL3 (80%:15%:5%) 30 nm |
| 88 | 10 nm | M4:M2:PtL4 (70%:25%:5%) 30 nm |
| 89 | — | M1:M2:PtL5 (75%:20%:5%) 30 nm |
| 90 | — | M1:M2:PtL6 (80%:15%:5%) 30 nm |

TABLE 1-continued

Use of compounds according to the invention as emitters in phosphorescent OLEDs

| Ex. | EBL | EML/thickness |
|---|---|---|
| 91 | 10 nm | M4:M2:PtL7 (70%:25%:5%) 30 nm |
| 92 | — | M1:M2:PtL8 (80%:15%:5%) 30 nm |
| 93 | 10 nm | M4:M2:PtL9 (75%:20%:5%) 30 nm |
| 94 | 10 nm | M4:M2:PtL10 (70%:25%:5%) 30 nm |
| 95 | 10 nm | M4:M2:PtL11 (70%:25%:5%) 30 nm |
| 96 | — | M1:M2:PtL12 (80%:15%:5%) 30 nm |
| 97 | — | M1:M2:PtL13 (80%:15%:5%) 30 nm |
| 98 | — | M1:PtL14 (85%:15%) 30 nm |
| 99 | — | M1:M2:PtL15 (80%:15%:5%) 30 nm |
| 100 | — | M1:M2:PtL16 (80%:15%:5%) 30 nm |
| 101 | 10 nm | M4:M2:PtL17 (75%:20%:5%) 30 nm |
| 102 | 10 nm | M4:M2:PtL18 (60%:35%:5%) 30 nm |
| 103 | — | M1:M2:PtL19 (80%:15%:5%) 30 nm |
| 104 | — | M1:M2:PtL20 (80%:15%:5%) 30 nm |
| 105 | — | M1:M2:PtL21 (80%:10%:10%) 30 nm |
| 106 | — | M1:M2:PtL22 (80%:15%:5%) 30 nm |
| 107 | — | M1:M2:PtL23 (80%:15%:5%) 30 nm |
| 108 | 10 nm | M4:M2:PtL24 (65%:30%:5%) 30 nm |
| 109 | 10 nm | M4:M2:PtL25 (60%:35%:5%) 30 nm |
| 110 | 10 nm | M4:M2:PtL26 (60%:35%:5%) 30 nm |
| 111 | — | M1:M2:PtL27 (80%:15%:5%) 30 nm |
| 112 | — | M1:M2:PtL28 (80%:15%:5%) 30 nm |
| 113 | — | M1:M2:PtL29 (80%:15%:5%) 30 nm |
| 114 | — | M1:M2:PtL30 (80%:15%:5%) 30 nm |
| 115 | 10 nm | M4:M2:PtL31 (60%:35%:5%) 30 nm |

TABLE 1-continued

Use of compounds according to the invention as emitters in phosphorescent OLEDs

| Ex. | EBL | EML/thickness |
|---|---|---|
| 116 | 10 nm | M4:M2:PtL32 (60%:35%:5%) 30 nm |

TABLE 2

Use of compounds according to the invention as emitters in phosphorescent OLEDs

| Ex. | EQE [%] at 1000 cd/m$^2$ | Voltage (V) at 1000 cd/m$^2$ | CIE x/y at 1000 cd/m$^2$ | LT50 (h) at 1000 cd/m$^2$ |
|---|---|---|---|---|
| 85 | 20.0 | 3.4 | 0.32/0.64 | 800 |
| 86 | 20.3 | 3.3 | 0.32/0.64 | 34000 |
| 87 | 20.7 | 3.6 | 0.32/0.64 | 38000 |
| 88 | 14.0 | 4.8 | 0.15/0.24 | 800 |
| 89 | 18.9 | 3.5 | 0.32/0.64 | 18000 |
| 90 | 20.2 | 3.6 | 0.32/0.64 | 45000 |
| 91 | 14.8 | 4.3 | 0.16/0.27 | — |
| 92 | 18.6 | 3.5 | 0.27/0.58 | 27000 |
| 93 | 18.1 | 4.3 | 0.16/0.34 | — |
| 94 | 13.5 | 4.6 | 0.15/0.26 | 1600 |
| 95 | 12.9 | 4.9 | 0.15/0.24 | — |
| 96 | 19.6 | 3.6 | 0.33/0.63 | 37000 |
| 97 | 14.8 | 3.5 | 0.68/0.32 | 25000 |
| 98 | 19.9 | 3.5 | 0.32/0.64 | 41000 |
| 99 | 21.0 | 3.6 | 0.32/0.64 | 43000 |
| 100 | 20.4 | 4.2 | 0.32/0.64 | 40000 |
| 101 | 16.2 | 4.3 | 0.16/0.27 | — |
| 102 | 13.4 | 4.8 | 0.15/0.25 | — |
| 103 | 18.8 | 3.7 | 0.32/0.64 | 29000 |
| 104 | 16.0 | 4.6 | 0.29/0.59 | — |
| 105 | 11.2 | 3.5 | 0.68/0.32 | 17000 |
| 106 | 14.5 | 3.6 | 0.68/0.32 | — |
| 107 | 21.4 | 3.5 | 0.33/0.63 | 44000 |
| 108 | 20.4 | 3.5 | 0.33/0.63 | 45000 |
| 109 | 11.5 | 4.5 | 0.16/0.28 | 1100 |
| 110 | 18.5 | 3.7 | 0.33/0.63 | 30000 |
| 111 | 20.4 | 4.0 | 0.33/0.63 | 39000 |
| 112 | 20.8 | 3.6 | 0.26/0.63 | 54000 |
| 113 | 21.0 | 3.7 | 0.26/0.63 | 52000 |
| 114 | 20.3 | 3.4 | 0.25/0.62 | 55000 |
| 115 | 12.0 | 4.6 | 0.15/0.25 | — |
| 116 | 11.8 | 5.3 | 0.15/0.22 | — |

TABLE 3

Structural formulae of the materials used

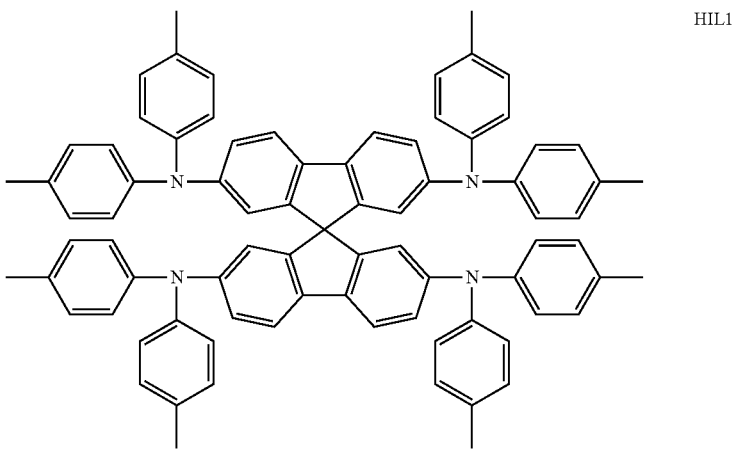

HIL1

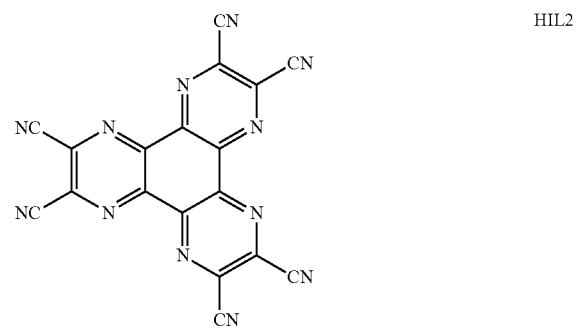

HIL2

TABLE 3-continued
Structural formulae of the materials used
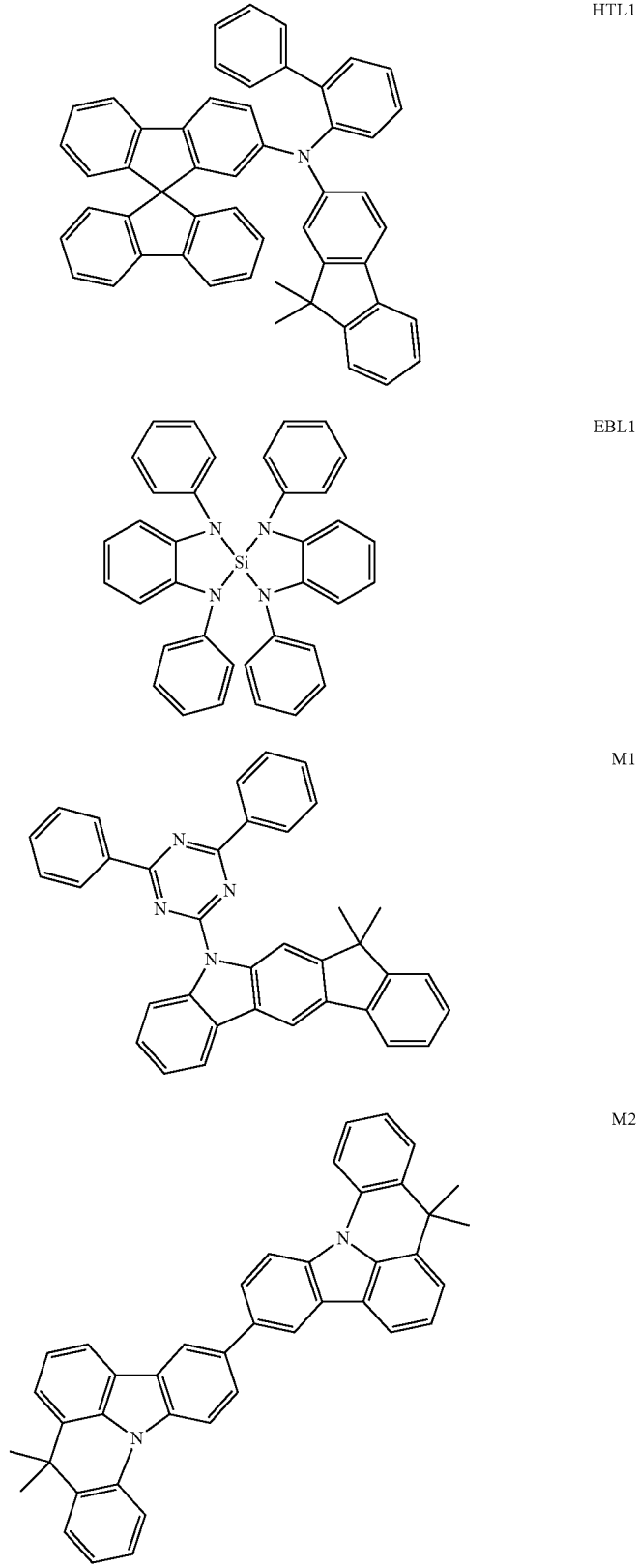
HTL1
EBL1
M1
M2

TABLE 3-continued
Structural formulae of the materials used
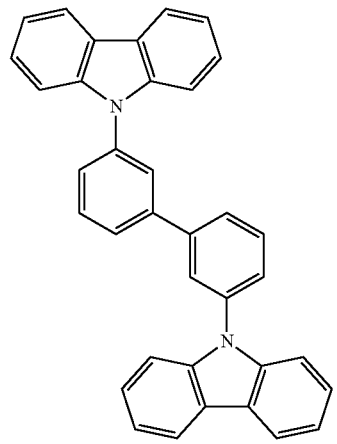 [SMILES: c1cc(-c2cccc(-n3c4ccccc4c4ccccc43)c2)cc(-n2c3ccccc3c3ccccc32)c1]
M3
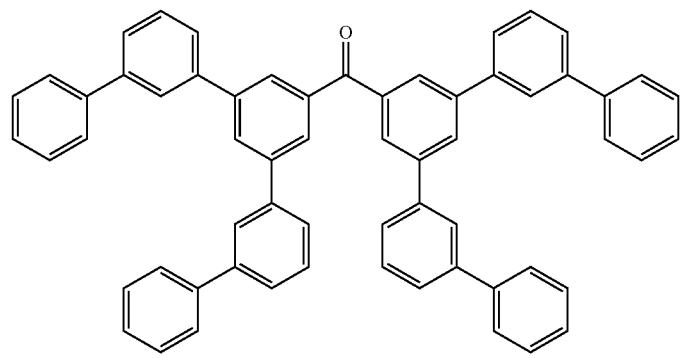 [SMILES: O=C(c1cc(-c2cccc(-c3ccccc3)c2)cc(-c2cccc(-c3ccccc3)c2)c1)c1cc(-c2cccc(-c3ccccc3)c2)cc(-c2cccc(-c3ccccc3)c2)c1]
M4
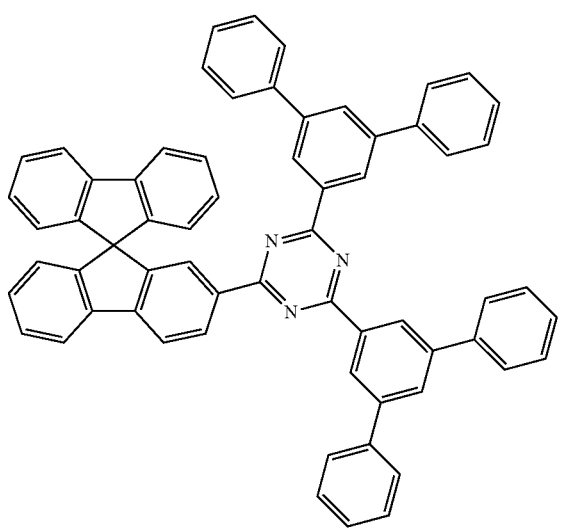 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1
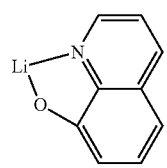
LiQ

The invention claimed is:
1. A compound of the formula (1),

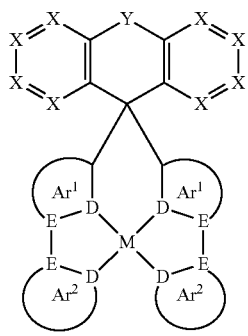

formula (1)

where the following applies to the symbols used:
M is selected on each occurrence, identically or differently, from the group consisting of platinum, palladium, nickel, rhodium, iridium and gold;
X is on each occurrence, identically or differently, $CR^1$ or N;
Y is C=O, BR, $SiR_2$, NR, PR, P(=O)R, CR=CR, $CR_2$—$CR_2$ or CR=N; or Y stands for a group of the formula (2),

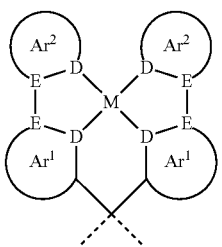

formula (2)

where the dashed bonds indicate the linking of this group;
D is on each occurrence, identically or differently, C or N;
E is C if the ring in which this E is bonded is an aromatic or heteroaromatic six-membered ring; or is C or N if the ring in which this E is bonded is a heteroaromatic five-membered ring;
$Ar^1$ is on each occurrence, identically or differently, together with D and E, an aryl or heteroaryl group comprising a five or six-membered aromatic ring having D and E as members of the ring, wherein the aryl or heteroaryl group is optionally substituted by one or more radicals $R^1$; adjacent groups $Ar^1$ and $Ar^2$ here may also be linked to one another by two radicals $R^1$, which are linked to one another, or by a group $CR^2$=N;
$Ar^2$ is on each occurrence, identically or differently, together with D and E, an aryl or heteroaryl group comprising a five or six-membered aromatic ring having D and E as members of the ring, wherein the aryl or heteroaryl group is optionally substituted by one or more radicals $R^1$; adjacent groups $Ar^2$ and $Ar^1$ here may also be linked to one another by two radicals $R^1$, which are linked to one another, or by a group $CR^2$=N;
R is on each occurrence, identically or differently, H, D, F, $N(R^2)_2$, CN, C(=O)$N(R^2)_2$, $Si(R^2)_3$, $B(OR^2)_2$, C(=O)$R^2$, P(=O)$(R^2)_2$, S(=O)$R^2$, $S(=O)_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C$=$CR^2$, C≡C, $Si(R^2)_2$, C=O, $NR^2$, O, S or $CONR^2$ and where one or more H atoms is optionally replaced by D, F, Cl, Br, I or CN, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$; two radicals R here which are bonded to the same C or Si atom may also form a mono- or polycyclic, aliphatic or aromatic ring system with one another;
$R^1$ is on each occurrence, identically or differently, H, D, F, Cl, Br, I, $N(R^2)_2$, CN, $NO_2$, OH, COOH, C(=O)$N(R^2)_2$, $Si(R^2)_3$, $B(OR^2)_2$, C(=O)$R^2$, P(=O)$(R^2)_2$, S(=O)$R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C$=$CR^2$, C≡C, $Si(R^2)_2$, C=O, $NR^2$, O, S or $CONR^2$ and where one or more H atoms is optionally replaced by D, F, Cl, Br, I or CN, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$; two adjacent radicals $R^1$ here may also form a mono- or polycyclic, aliphatic or aromatic ring system with one another; furthermore, the radicals $R^1$ which are bonded to adjacent groups $Ar^1$ and $Ar^2$ may also form a mono- or polycyclic, aliphatic or aromatic ring system with one another; furthermore, two radicals $R^1$ on the two groups $Ar^2$ may also form a ring system with one another;
$R^2$ is on each occurrence, identically or differently, H, D, F, Cl, Br, I, $N(R^3)_2$, CN, $NO_2$, $Si(R^3)_3$, $B(OR^3)_2$, C(=O)$R^3$, P(=O)$(R^3)_2$, S(=O)$R^3$, $S(=O)_2R^3$, $OSO_2R^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^3$, where one or more non-adjacent $CH_2$ groups is optionally replaced by $R^3C$=$CR^3$, C≡C, $Si(R^3)_2$, C=O, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which is optionally substituted by one or more radicals $R^3$, or an aralkyl or heteroaralkyl group having 5 to 40 aromatic ring atoms, which is optionally substituted by one or more radicals R³; two or more adjacent radicals R² here may form a mono- or polycyclic, aliphatic ring system with one another;

R³ is on each occurrence, identically or differently, H, D, F or an aliphatic, aromatic and/or heteroaromatic radical having 1 to 20 C atoms, in which, in addition, one or more H atoms is optionally replaced by F; two or more substituents R³ here may also form a mono- or polycyclic, aliphatic ring system with one another;

two groups Ar² here may also be bridged to one another by a group Y.

2. The compound according to claim 1, wherein M is selected from the group consisting of Pt(II), Pd(II), Ni(II), Rh(I), Ir(I) and Au(III).

3. The compound according to claim 1, wherein M is Pt(II).

4. The compound according to claim 1, wherein the compound is selected from the structures of the formula (3), (4), (5) or (6),

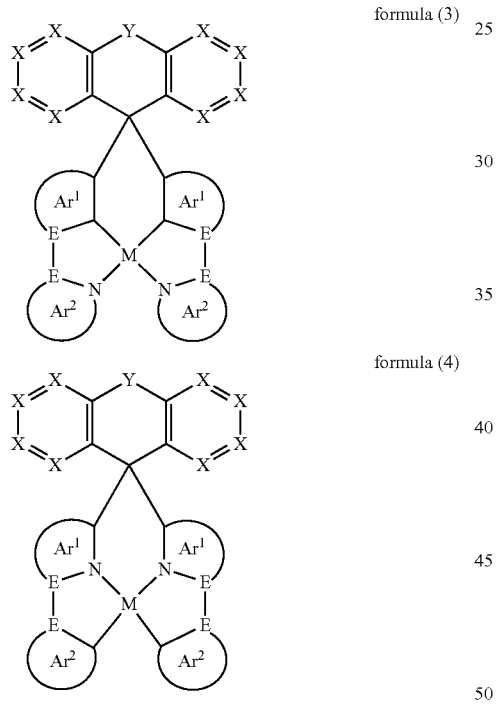

formula (3)

formula (4)

formula (5)

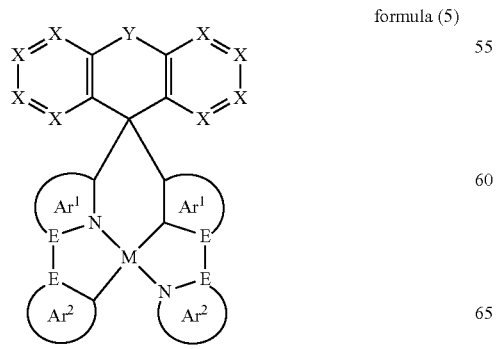

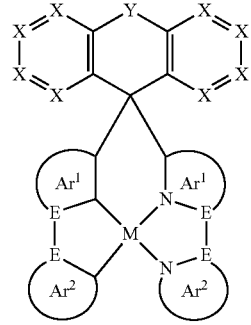

formula (6)

where the symbols used have the meanings given in claim 1.

5. The compound according to claim 1, wherein the compound is selected from the structures of the formulae (3a), (4a), (5a) and (6a),

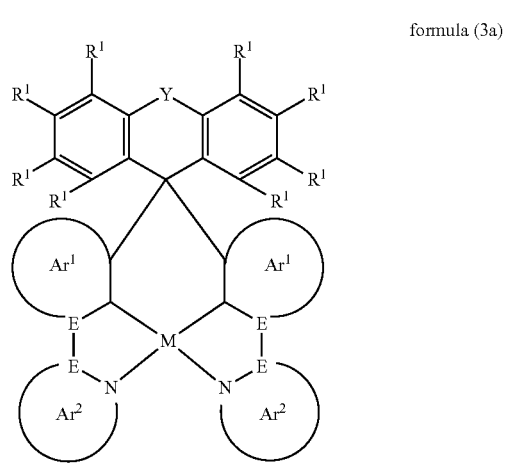

formula (3a)

formula (4a)

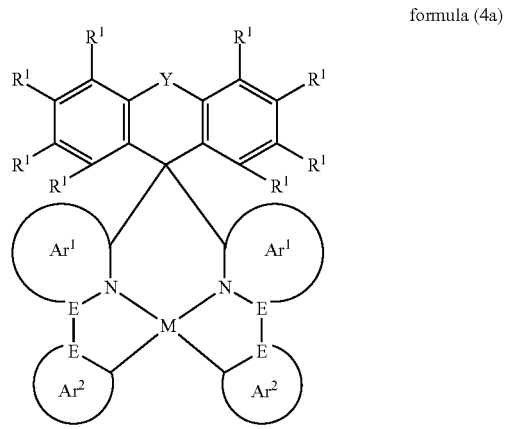

formula (5a)

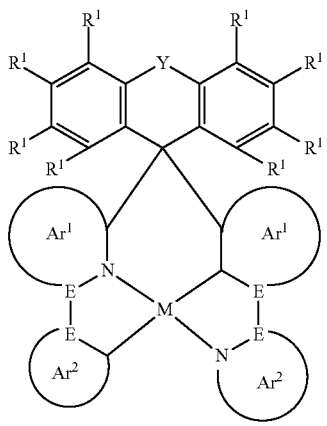

formula (6a)

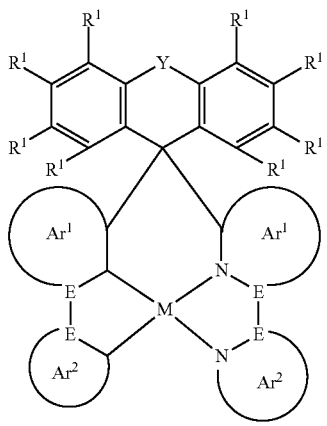

where R¹ stands for H.

6. The compound according to claim 1, wherein E stands for C.

7. The compound according to claim 1, wherein all groups Ar¹ are selected identically and are identically substituted and in that all groups Ar² are selected identically and are identically substituted.

8. The compound according to claim 1, wherein Ar¹ is selected, identically or differently on each occurrence, from the structures of the formulae (8), (10)-(12), (14), (16)-(17), (19)-(20), (24)-(26h), formula (8)

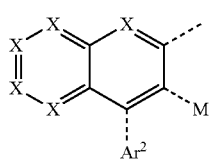

formula (10)

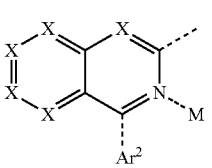

formula (11)

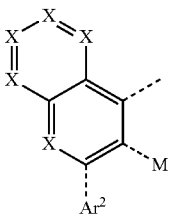

formula (12)

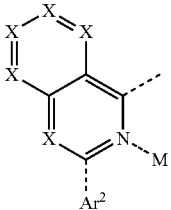

formula (14)

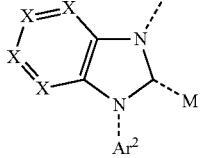

formula (14)

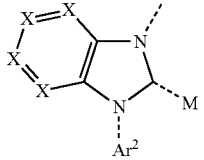

formula (16)

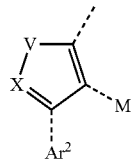

formula (17)

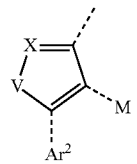

formula (19)

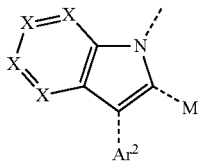

formula (20)

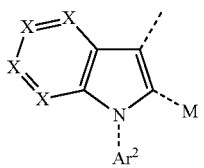

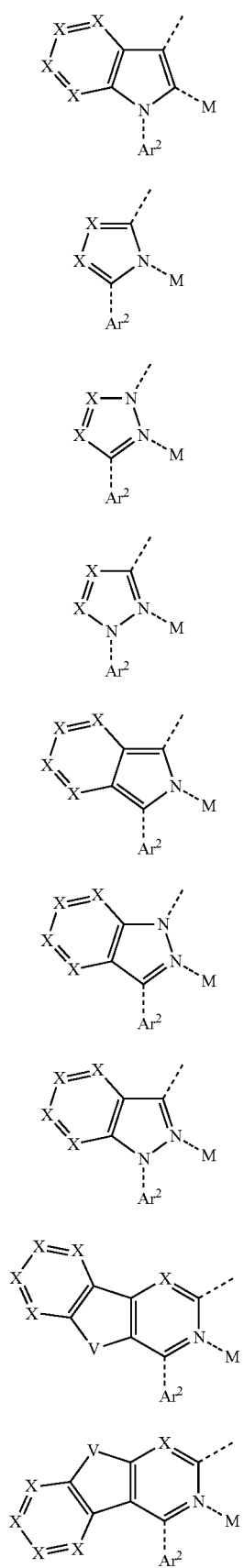
formula (20)
formula (21)
formula (22)
formula (23)
formula (24)
formula (25)
formula (26)
formula (26a)
formula (26b)
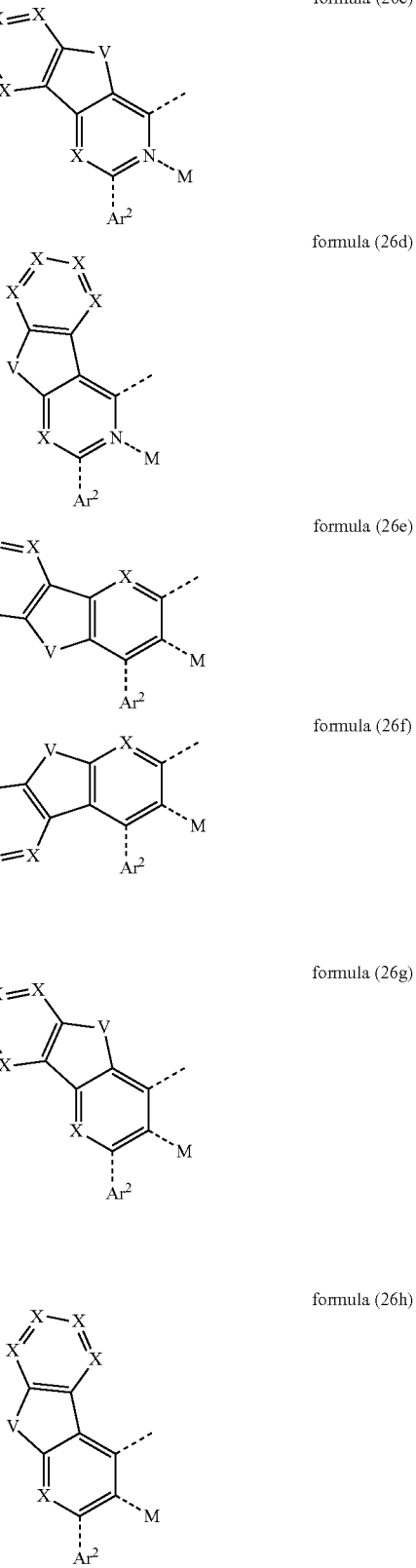
formula (26c)
formula (26d)
formula (26e)
formula (26f)
formula (26g)
formula (26h)
and in that Ar² is selected, identically or differently on each occurrence, from the structures of the formulae (28)-(30), (32)-(34), (36), (38)-(40) and (43)-(48d),

| | |
|---|---|
| formula (28) 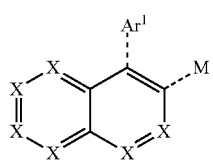 | formula (36) 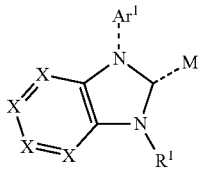 |
| formula (29) 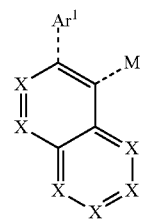 | formula (38) 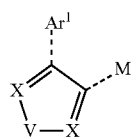 |
| | formula (39) 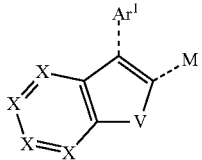 |
| formula (30) 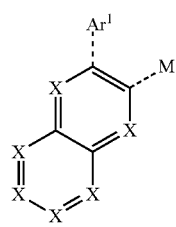 | formula (40) 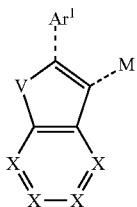 |
| formula (32) 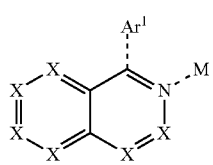 | |
| formula (33) 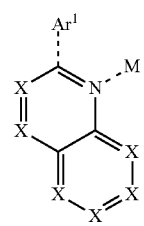 | formula (43) 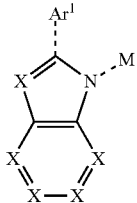 |
| formula (34) 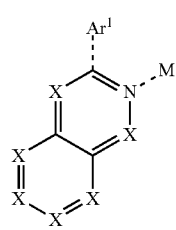 | formula (43) 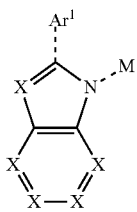 |
| formula (34) 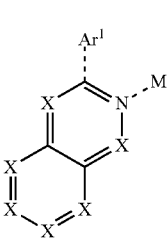 | formula (44) 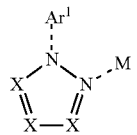 |
| | formula (45) |

-continued formula (46)
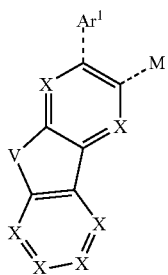

formula (47)
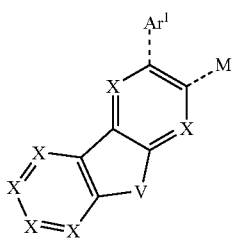

formula (48)
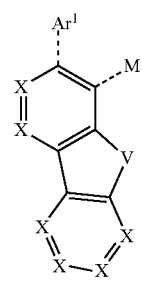

formula (48a)
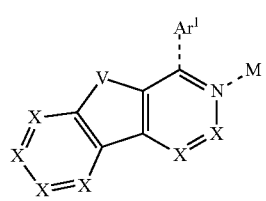

formula (48b)
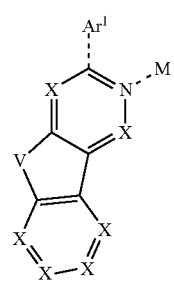

formula (48c)
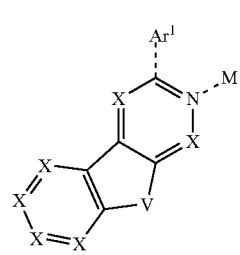

-continued formula (48d)
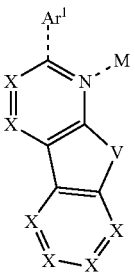

where the bond to the carbon atom of the bridgehead, to M and to $Ar^1$ or to $Ar^2$ is in each case indicated by dashed bonds and X and $R^1$ having the meaning given in claim 1; V stands on each occurrence, identically or differently, for O, S, $NR^1$ or $C(R^1)_2$.

9. The compound according to claim 1, wherein adjacent groups $Ar^1$ and $Ar^2$ form a ring with one another, where the ring closure takes place via a group $CR^2$=$CR^2$, $CR^2$=N, $C(R^2)_2$—$C(R^2)_2$, C(=O)—O or C(=O)—$NR^2$.

10. The compound according to claim 1, wherein one or both groups $Ar^1$-$Ar^2$ are selected from the groups of the formulae (51) to (59), formula (51)
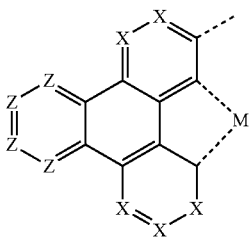

formula (52)
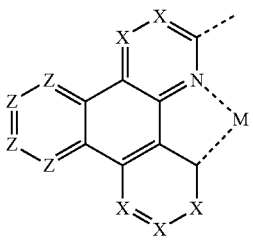

formula (53)
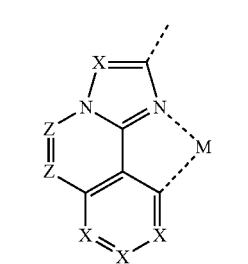

-continued formula (54)
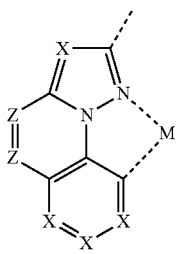
Formel (51)

formula (55)
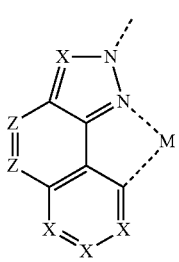

formula (56)
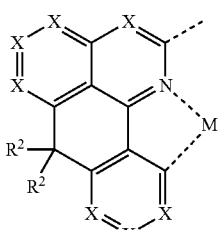

formula (57)
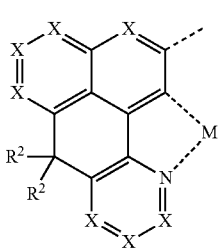

formula (58)
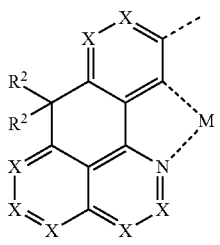

formula (59)
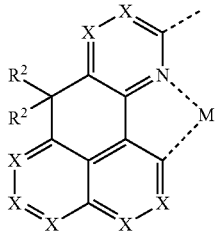

where the bond to the metal or to the bridgehead carbon atom are in each case indicated by dashed bonds, Z stands on each occurrence, identically or differently, for $CR^2$ or N, where a maximum of one group Z stands for N, and the other symbols have the meanings given in claim 1.

11. A process for the preparation of the compound according to claim 1, which comprises reacting the corresponding ligand with a metal starting material.

12. A formulation comprising at least one compound according to claim 1 and at least one solvent.

13. The formulation according to claim 12, wherein the formulation is a solution or a suspension.

14. An electronic device comprising the compound according to claim 1.

15. The electronic device as claimed in claim 14, wherein the device is selected from the group consisting of an organic electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell and an organic laser diode.

16. An organic electroluminescent device which comprises employing the compound according to claim 1 as emitting compound in one or more emitting layers.

17. An electronic device which comprises the compound according to claim 1 employed in combination with one or more matrix materials.

18. The electronic device according to claim 17, wherein said one or more matrix materials, is selected from the group consisting of ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives, zinc complexes, dibenzofuran derivatives and bridged carbazole derivatives.

19. The compound according to claim 1, wherein the compound is uncharged and the following furthermore applies:

M is selected from the group consisting of Pt(II), Pd(II), Ni(II), Rh(I), Ir(I) and Au(III);

Y is selected from the group consisting of C=O and NR;

X is, identically or differently on each occurrence, $CR^1$ or N, wherein a maximum of two symbols X per ring stand for N and the other symbols X stand for $CR^1$;

$Ar^1$ is selected, identically or differently on each occurrence, from the structures of the formulae (8), (10)-(12), (14), (16)-(17), (19)-(20), (24)-(26h);

formula (8)
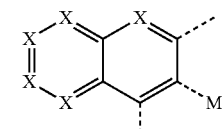

formula (10)
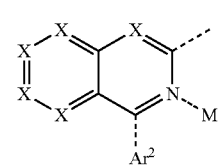

formula (11)
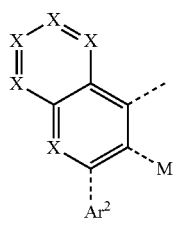
formula (12)
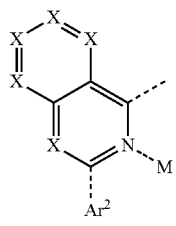
formula (14)
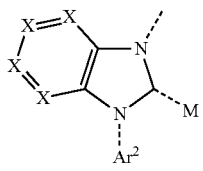
formula (16)
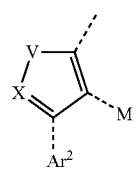
formula (17)
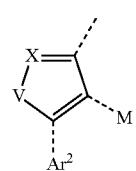
formula (19)
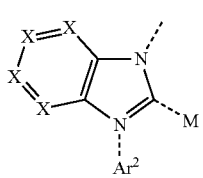
formula (20)
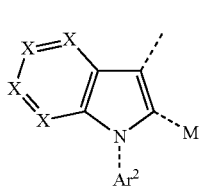
formula (24)
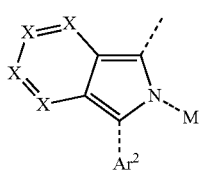
formula (25)
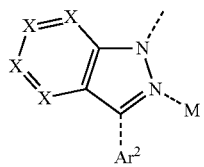
formula (26)
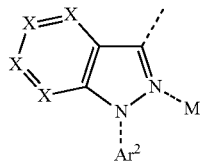
formula (26a)
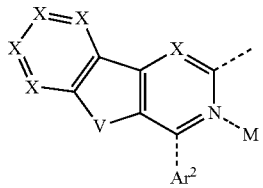
formula (26b)
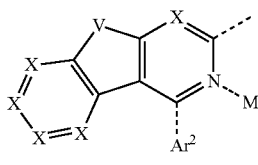
formula (26c)
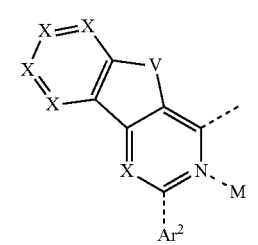
formula (26d)
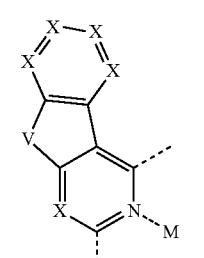
formula (26e)
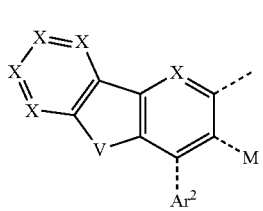
formula (26f)
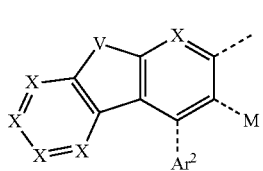

formula (26g)
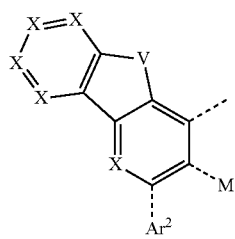
formula (26h)
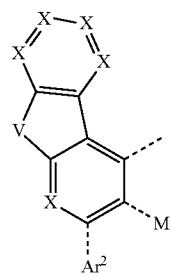
Ar² is selected, identically or differently on each occurrence, from the structures of the formulae (28)-(30), (32)-(34), (36), (38)-(40) and (43)-(48d);
formula (28)
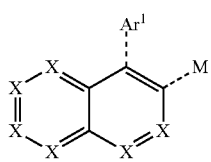
formula (29)
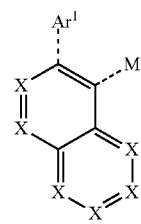
formula (30)
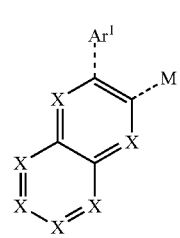
formula (32)
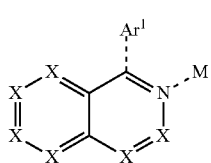
formula (33)
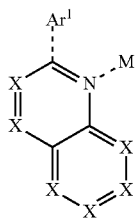
formula (34)
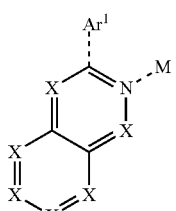
formula (36)
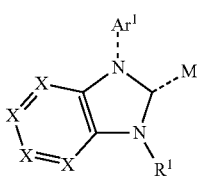
formula (38)
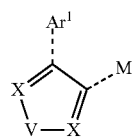
formula (39)
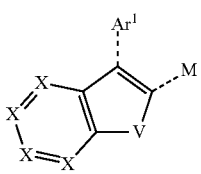
formula (40)
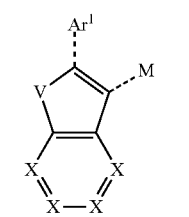
formula (43)
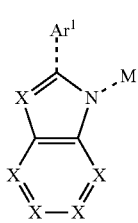
formula (44)
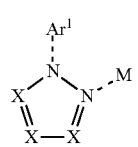

-continued
formula (45)
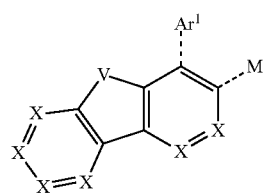
formula (46)
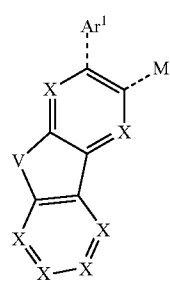
formula (47)
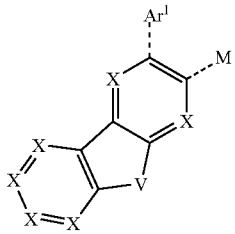
formula (48)
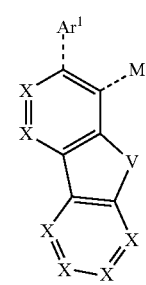
formula (48a)
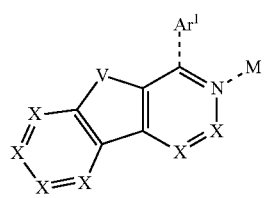
formula (48b)
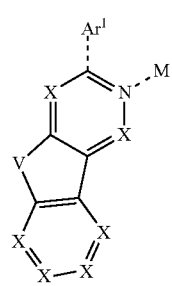
-continued
formula (48c)
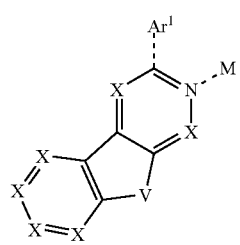
formula (48d)
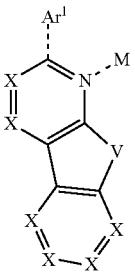
or
Ar$^1$-Ar$^2$ is selected, identically or differently on each occurrence, from the structures of the formulae (51) to (59)
formula (51)
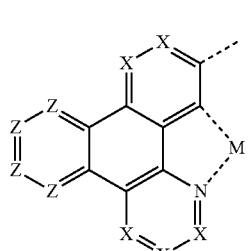
formula (52)
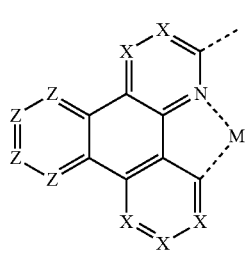
formula (53)
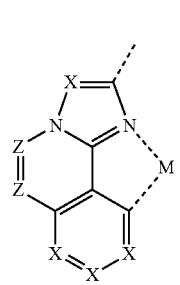

-continued

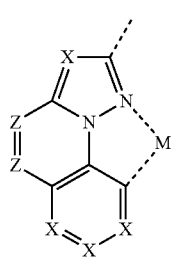
formula (54)

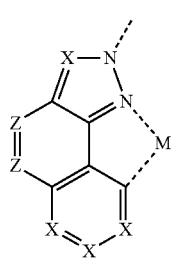
formula (55)

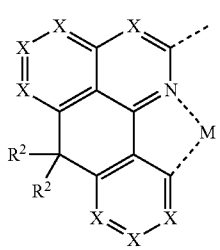
formula (56)

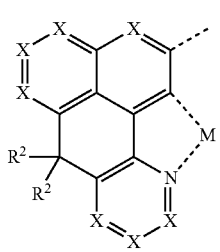
formula (57)

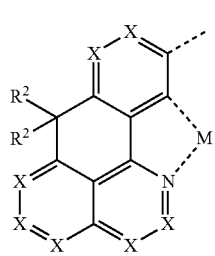
formula (58)

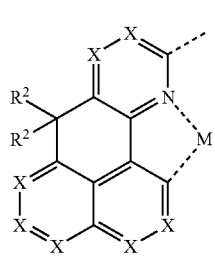
formula (59)

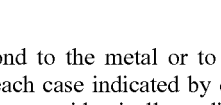

where the bond to the metal or to the bridgehead carbon atom are in each case indicated by dashed bonds, Z stands on each occurrence, identically or differently, for $CR^2$ or N, where a maximum of one group Z stands for N;

$R^1$ is selected on each occurrence, identically or differently, from the group consisting of H, D, F, $N(R^2)_2$, CN, $C(=O)R^2$, a straight-chain alkyl group having 1 to 10 C atoms or an alkenyl group having 2 to 10 C atoms or a branched or cyclic alkyl group having 3 to 10 C atoms, each of which is optionally substituted by one or more radicals $R^2$, where one or more H atoms is optionally replaced by D or F, or an aromatic or heteroaromatic ring system having 5 to 30 aromatic ring atoms, which may in each case be substituted by one or more radicals $R^2$;

R stands for an aromatic or heteroaromatic ring system having 5 to 18 aromatic ring atoms, which may in each case be substituted by one or more radicals $R^2$ and which contains no condensed aryl or heteroaryl groups.

20. The compound according to claim 1, wherein $Ar^1$ is selected, identically or differently on each occurrence, from the structures of the formulae (7), (9), (13), (15), (18) and (21)-(23),

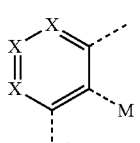
formula (7)

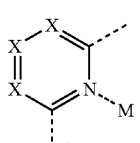
formula (9)

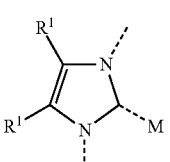
formula (13)

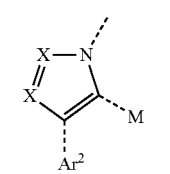
formula (15)

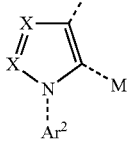
formula (18)

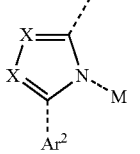
formula (21)

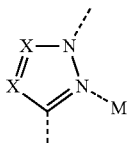
formula (22)

-continued formula (23)

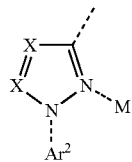

and in that Ar² is selected, identically or differently on each occurrence, from the structures of the formulae (27), (31), (35), (37), (41), (42), (49) and (50) (41) and (42)

formula (27)

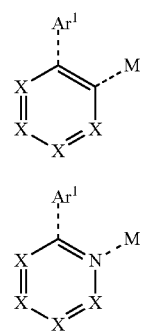

formula (31)

formula (35)

formula (37)

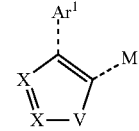

formula (41)

-continued formula (42)

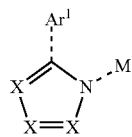

or Ar¹-Ar² is selected, identically or differently on each occurrence, from the structures of the formulae (49) and (50)

formula (49)

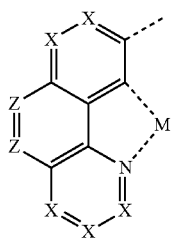

formula (50)

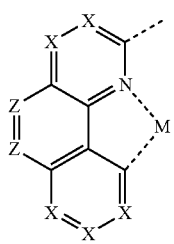

where the bond to the carbon atom of the bridgehead, to M and to Ar¹ or to Ar² is in each case indicated by dashed bonds and X and R¹ having the meaning given in claim 1; V stands on each occurrence, identically or differently, for O, S, NR¹ or C(R¹)₂; and Z stands on each occurrence, identically or differently, for CR² or N, where a maximum of one group Z stands for N.

\* \* \* \* \*